US007087661B1

(12) United States Patent
Alberte et al.

(10) Patent No.: US 7,087,661 B1
(45) Date of Patent: Aug. 8, 2006

(54) SAFE AND EFFECTIVE BIOFILM INHIBITORY COMPOUNDS AND HEALTH-RELATED USES THEREOF

(75) Inventors: Randall S. Alberte, Falmouth, ME (US); Richard C. Zimmerman, Pacific Grove, CA (US)

(73) Assignee: Cernofina, LLC, Fort Meyers, FL (US)

( * ) Notice: Subject to any disclaimer, the term of this patent is extended or adjusted under 35 U.S.C. 154(b) by 0 days.

(21) Appl. No.: 09/405,269

(22) Filed: Sep. 23, 1999

Related U.S. Application Data

(63) Continuation-in-part of application No. 09/159,814, filed on Sep. 23, 1998, now abandoned.

(51) Int. Cl.
*A01N 31/00* (2006.01)
*A01N 41/02* (2006.01)
*A01P 1/00* (2006.01)
*A01P 3/00* (2006.01)

(52) U.S. Cl. .............. 523/122; 524/156; 524/158; 524/165; 558/20; 558/37; 568/28; 568/74; 424/405; 424/407; 424/408; 424/409; 424/457; 424/484; 424/489

(58) Field of Classification Search ............ 424/422; 428/411.1, 704, 543; 427/2.12, 2.24, 2.28, 427/2.29, 2.3, 2.31; 558/20, 37, 38
See application file for complete search history.

(56) References Cited

U.S. PATENT DOCUMENTS

| | | | | |
|---|---|---|---|---|
| 2,190,733 | A * | 2/1940 | Richmond | 558/37 |
| 3,133,949 | A * | 5/1964 | Rutkowski et al. | 558/36 |
| 3,632,416 | A * | 1/1972 | Shepherd et al. | |
| 4,046,731 | A | 9/1977 | Mortimer et al. | |
| 4,240,163 | A * | 12/1980 | Galin | |
| 4,243,549 | A | 1/1981 | Messenger et al. | 516/25 |
| 4,281,110 | A | 7/1981 | Blount | |
| 4,605,564 | A | 8/1986 | Kulla et al. | 427/2 |
| 4,895,566 | A | 1/1990 | Lee | 604/266 |
| 5,019,096 | A | 5/1991 | Fox, Jr. et al. | 623/1 |
| 5,057,533 | A * | 10/1991 | Tanaka et al. | 514/396 |
| 5,066,706 | A | 11/1991 | Destryker et al. | |
| 5,089,205 | A | 2/1992 | Huang et al. | 264/255 |
| 5,292,532 | A * | 3/1994 | Bombart | 424/405 |
| 5,312,642 | A * | 5/1994 | Chesterfield et al. | |
| 5,328,954 | A | 7/1994 | Sarangapani | 524/589 |
| 5,384,176 | A | 1/1995 | Zimmerman et al. | 428/68 |
| 5,436,008 | A * | 7/1995 | Richter et al. | 424/405 |
| 5,607,741 | A | 3/1997 | Zimmerman et al. | 428/68 |
| 5,681,575 | A | 10/1997 | Burrell et al. | 424/423 |
| 5,688,516 | A | 11/1997 | Raad et al. | 424/409 |
| 5,753,251 | A | 5/1998 | Burrell et al. | 424/426 |
| 5,770,255 | A | 6/1998 | Burrell et al. | 427/2.1 |
| 5,833,963 | A * | 11/1998 | Mackles et al. | 424/65 |
| 5,853,745 | A | 12/1998 | Darouiche | 424/423 |
| 5,877,243 | A | 3/1999 | Sarangapani | 524/139 |
| 5,902,283 | A | 5/1999 | Darouiche et al. | 604/265 |

FOREIGN PATENT DOCUMENTS

| | | |
|---|---|---|
| BE | 624917 | 3/1963 |
| DE | 32 29 097 A1 | 2/1984 |
| EP | 0328421 B1 | 8/1989 |
| EP | 0372130 | 6/1990 |
| EP | 626854 B1 | 12/1994 |
| EP | 0641224 B1 | 3/1995 |
| EP | 0761243 A1 | 3/1997 |
| FR | 1. 696 M | 2/1963 |
| FR | 2443837 | 7/1980 |
| GB | 207250BA | 10/1981 |
| JP | 04279531 | 10/1992 |
| WO | WO 94/13462 | 6/1994 |
| WO | WO 96/09761 | 4/1996 |
| WO | WO 98/09667 | 3/1998 |
| WO | WO 98/50461 | 11/1998 |

OTHER PUBLICATIONS

The Merck Index, Tenth Ed., pp. 876-877, Merck & Co., Inc., Rahway, N.J., U.S.A. (1983).*
Singer, Adam, Cutaneous Wound Healing, The New England Journal of Medicine, p. 738-746, Sep. 2, 1999.
International Search Report for PCT/US 99/22235, dated Mar. 3, 2000.
Afinogenov and Panarin; "Alkyl Sulfates and Alkylarylsulfonates as Penicillinase Inhibitors", Antibiotiki (Moscow) 21(10): 876-880 (1976)(Abstract), (no month).
Anan'eva et al.; "Effect of Surfactants on Staphylococcal Plasmocoagulase", Zh. Mikrobiol. Immunobiol., 6: 111-115 (1977) (Abstract), (no month).
Elinov and Afinogenov; "Effect of Sulfonol and Alkyl Sulfate on Penicillin Resistant Staphylococci Separated from Bone Wounds", Tr. Leningrad. Khim.-Farm. Inst., 27: 64-72 (1969) (Abstract No. 20F835), (no month).
Panarin et al.; "Mechanism of Penicillinase Inhibition by Alkyl Sulfates in the Presence of Synthetic Polyelectrolytes", Antibiotiki (Moscow) 22(6): 502-506 (1977) (Abstract), (no month).

(Continued)

Primary Examiner—Marie Yamnitzky
(74) Attorney, Agent, or Firm—Foley Hoag LLP

(57) ABSTRACT

The present invention provides compounds and materials that reduce the accumulation of microorganisms a surface, by interfering with the attachment of the organisms to the surface. The compounds and materials are thus useful in preventing the formation of biofilms on surfaces in health-related environments. By preventing the formation of biofilms, the compounds formulated according to the present invention can be used in the fabrication of grafts, implants, medical devices in order to prevent infection thereof. The compounds formulated according to the present invention display an additional anticoagulant property, permitting their use in settings where decrease in blood coagulability is desirable.

7 Claims, 9 Drawing Sheets

OTHER PUBLICATIONS

Panarin and Afinogenov; "Relation Between Structure and Antimicrobial Activity in Alkyl Sulfates", Khim. Farm. Zh. 12(1); 79-81 (1978) (Abstract), (no month).

Todd et al.; "The Antifouling Activity of Natural and Synthetic Phenolic Acid Sulphate Esters", Phytochemistry 34(2): 401-404 (1993), (no month).

* cited by examiner

SAFE AND EFFECTIVE BIOFILM INHIBITORY COMPOUNDS AND HEALTH-RELATED USES THEREOF

RELATED APPLICATIONS

This application is a continuation-in-part of U.S. patent application Ser. No. 09/159,814, filed Sep. 23, 1998, now abandoned.

BACKGROUND OF THE INVENTION

Infection is a frequent complication of many invasive surgical, therapeutic and diagnostic procedures. For procedures involving implantable medical devices, avoiding infection can be particularly problematic because biofilms can develop which protect the microbes from clearing by the subject's immune system. As these infections are difficult to treat with antibiotics, removal of the device is often necessitated, which is traumatic to the patient and increases the medical cost.

Any material left embedded in the body provides a surface for accumulation of infectious microorganisms, particularly bacteria and occasionally fungi. This is understood to take place through the formation of biofilms. A biofilm is a type of fouling that occurs when microorganisms attach to surfaces and secrete a hydrated polymeric matrix that surrounds them. Microorganisms existing in a biofilm, termed sessile, grow in a protected environment that insulates them from attack from antimicrobial agents. These sessile communities can give rise to nonsessile individuals, termed planktonic, which rapidly multiply and disperse. These planktonic organisms are responsible for invasive and disseminated infections. They are the targets of antimicrobial therapy. Conventional treatments fail to eradicate the sessile communities rooted in the biofilm. Biofilms are understood to be a frequently occurring reservoir for infectious agents. The biology of biofilms is described in more detail in "Bacterial biofilms: a common cause of persistent infection," J. Costerson, P. Stewart, E. Greenberg, Science 284: 1318–1322 (1999), incorporated herein by reference.

Biofilms develop preferentially on inert surfaces or on non-living tissue, and occur commonly on medical devices and devascularized or dead tissues. Biofilms have been identified on sequestra of dead bone and on bone grafts, from which they can incite an invasive infection called osteomyelitis that can kill even more bone. Biofilms have been also identified on living, hypovascular tissues such as native heart valves, where they are responsible for the devastating infection called endocarditis where the microorganism not only can colonize distant locations by seeding throughout the bloodstream, but also can destroy the heart valve itself. Infections involving implanted medical devices generally involve biofilms, where a sessile community provides a reservoir for an invasive infection. The presence of microorganisms in a biofilm on a medical device represents contamination of that foreign body. The elicitation by the biofilm of clinically perceptible host responses constitutes an infection.

The development of an infection from an area of contamination is consistent with the natural history of biofilm growth and development. Biofilms grow slowly, in one or more locations, colonized by one or a plurality of microorganisms. The pattern of biofilm development involves initial attachment of a microorganism to a solid surface, the formation of microcolonies attached to the surface, and finally the differentiation of the microcolonies into exopolysaccharide-encased mature biofilms. Planktonic cells are released from biofilms in a natural pattern of programmed detachment, so that the biofilm serves as a nidus for multiple, recurrent acute invasive infections. Antibiotics typically treat the infection caused by the planktonic organisms, but fail to kill those sessile organisms protected in the biofilm.

Sessile microorganisms also give rise to localized symptoms, releasing antigens and stimulating antibody production that activates the immune system to attack the biofilm and the area surrounding it. Antibodies and host immune defenses are ineffective in killing the organisms in the biofilm, even though these organisms have elicited the antibody and related immune response. The cytotoxic products of the host's immunologically activated cells can be directed towards the host's own tissues. This phenomenon is seen in the mouth, where the host's response to the dental biofilm can inflame tissues surrounding the teeth and give rise to periodontitis. This phenomenon can also give rise to local inflammation around implanted medical devices and bone resorption with loosening of orthopedic and dental implants.

While host defenses may hold invasive infections in check by controlling the proliferation of planktonic organisms, this favorable equilibrium presupposes an intact immune system. Many patients in a hospital setting have compromised immune systems, rendering them more vulnerable to invasive infections once a biofilm community has become established. Patients requiring implantable medical devices may likewise have compromised immune systems, whether on a short-term or long-term basis. A poorly functioning immune system puts the host at greater risk for initial formation of a contaminated biofilm around a medical device and for the invasion of planktonic organisms into the surrounding tissues and the system. Once the planktonic organisms mount a full-scale infection, the immunocompromised host will be less likely to contain and control it, with potentially lethal results.

Protected from antibiotic treatment and host defenses, the microorganisms in a biofilm typically cause recurrent infections and low-grade local symptoms. The biofilm, once established, can only be eradicated surgically. When a foreign object becomes contaminated with microorganisms, the only way to eliminate local and systemic infection may be to remove the contaminated foreign article. If the material being removed is essential for health, a similar article may need to be replaced in the same location; the replacement article will be especially prone to infection because of the residual microorganisms in the area.

Since the difficulties associated with eliminating biofilm-based infections are well-recognized, a number of technologies have developed to treat surfaces or fluids bathing surfaces to prevent or impair biofilm formation. Biofilms adversely affect medical systems and other systems essential to public health such as water supplies and food production facilities. A number of technologies have been proposed that treat surfaces with organic or inorganic materials to interfere with biofilm development. For example, various methods have been employed to coat the surfaces of medical devices with antibiotics (See e.g. U.S. Pat. Nos. 4,107,121, 4,442, 133, 4,895,566, 4,917,686, 5,013,306, 4,952,419, 5,853,745 and 5,902,283) and other bacteriostatic compounds (See e.g U.S. Pat. Nos. 4,605,564, 4,886,505, 5,019,096, 5,295,979, 5,328,954, 5,681,575, 5,753,251, 5,770,255, and 5,877,243). Despite these technologies, contamination of medical devices and invasive infection therefrom continues to be a problem.

Infectious organisms are ubiquitous in the medical environment, despite vigorous efforts to maintain antisepsis. The presence of these organisms can result in infection of hospitalized patients and medical personnel. These infections, termed nosocomial, often involve organisms more virulent and more unusual than those encountered outside the hospital. In addition, hospital-acquired infections are more likely to involve organisms that have developed resistance to a number of antibiotics. Although cleansing and anti-bacterial regimens are routinely employed, infectious organisms readily colonize a variety of surfaces in the medical environment, especially those surfaces exposed to moisture or immersed in fluid. Even barrier materials, such as gloves, aprons and shields, can spread infection to the wearer or to others in the medical environment. Despite sterilization and cleansing, a variety of metallic and non-metallic materials in the medical environment can retain dangerous organisms trapped in a biofilm, thence to be passed on to other hosts.

Any agent used to impair biofilm formation in the medical environment must be safe to the user. Certain biocidal agents, in quantities sufficient to interfere with biofilms, also can damage host tissues. Antibiotics introduced into local tissue areas can induce the formation of resistant organisms which can then form biofilm communities whose planktonic microorganisms would likewise be resistant to the particular antibiotics. Any anti-biofilm or antifouling agent must furthermore not interfere with the salubrious characteristics of a medical device. Certain materials are selected to have a particular type of operator manipulability, softness, water-tightness, tensile strength or compressive durability, characteristics that cannot be altered by an agent added for anti-microbial effects.

As a further problem, it is possible that materials added to the surfaces of implantable devices to inhibit contamination and biofilm formation may be thrombogenic. Some implantable materials are of themselves thrombogenic. For example, it has been shown that contact with metal, glass, plastic or other similar surfaces can induce blood to clot. Heparin compounds, which are known to have anticoagulant effects, have therefore been applied to certain medical devices prior to implantation. However, there are few known products in the medical arsenal whose antimicrobial effects are combined with antithrombogenic effects. This combination would be particularly valuable to treat those medical devices that reside in the bloodstream, such as heart valves, artificial pumping devices ("artificial hearts" or left ventricular assist devices), vascular grafting prostheses and vascular stents. In these settings, clot formation can obstruct the flow of blood through the conduit and can furthermore break off pieces called emboli that are carried downstream, potentially blocking circulation to distant tissues or organs.

Biofilm formation has important public health implications. Drinking water systems are known to harbor biofilms, even though these environments often contain disinfectants. Any system providing an interface between a surface and a fluid has the potential for biofilm development. Water cooling towers for air conditioners are well-known to pose public health risks from biofilm formation, as episodic outbreaks of infections like Legionnaires' Disease attest. Turbulent fluid flow over the surface does not provide protection: biofilms can form in conduits where flowing water or other fluids pass, with the effects of altering flow characteristics and passing planktonic organisms downstream. Industrial fluid processing operations have experienced mechanical blockages, impedance of heat transfer processes, and biodeterioration of fluid-based industrial products, all attributable to biofilms. Biofilms have been identified in flow conduits like hemodialysis tubing, and in water distribution conduits. Biofilms have also been identified to cause biofouling in selected municipal water storage tanks, private wells and drip irrigation systems, unaffected by treatments with up to 200 ppm chlorine.

Biofilms are a constant problem in food processing environments. Food processing involves fluids, solid material and their combination. As an example, milk processing facilities provide fluid conduits and areas of fluid residence on surfaces. Cleansing milking and milk processing equipment presently utilizes interactions of mechanical, thermal and chemical processes in an air-injected clean-in-place methods. Additionally, the milk product itself is treated with pasteurization. In cheese producing, biofilms can lead to the production of calcium lactate crystals in Cheddar cheese. Meat processing and packing facilities are in like manner susceptible to biofilm formation. Non-metallic and metallic surfaces can be affected. Biofilms in meat processing facilities have been detected on rubber "fingers," plastic curtains, conveyor belt material, evisceration equipment and stainless steel surfaces. Controlling biofilms and microorganism contamination in food processing is hampered by the additional need that the agent used not affect the taste, texture or aesthetics of the product.

SUMMARY OF THE INVENTION

In one aspect, the instant invention features medical devices and products comprised of a compound having the general structure 1:

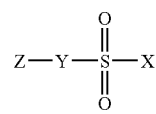

$$Z-Y-\overset{\overset{O}{\|}}{\underset{\underset{O}{\|}}{S}}-X \qquad 1$$

wherein

X represents —OH, —O(aryl), —O(acyl), —O(sulfonyl), —CN, F, Cl, or Br;

Y represents O, S, Se, or NR;

Z represents optionally substituted alkyl, heteroalkyl, cycloalkyl, heterocycloalkyl, aryl, heteroaryl, aralkyl, heteroaralkyl, or —(CH$_2$)$_m$—R$_{80}$;

R represents independently for each occurrence hydrogen, alkyl, heteroalkyl, aryl, heteroaryl, aralkyl, heteroaralkyl, or —(CH$_2$)$_m$—R$_{80}$;

R$_{80}$ represents independently for each occurrence aryl, cycloalkyl, cycloalkenyl, heterocyclyl, or polycyclyl; and m is an integer in the range 0 to 8 inclusive By interfering with the attachment of organisms to surfaces, the instant claimed medical devices and products have broad applicability in effectively inhibiting a variety of organisms.

In addition, medical devices that reside in the bloodstream and are comprised of the instant claimed compounds benefit from the combined antimicrobial and antithrombogenic effects of the compounds.

In addition, the compounds of the invention are relatively safe, even for widespread use, as they naturally degrade into carbon dioxide and water, or simple organic acids.

In addition, certain preferred compounds result in a constant or sustained release. Still other compounds have a relatively short half-life following release from a surface, rendering them particularly safe for widespread use. Yet other preferred compounds are readily synthesized.

Particularly preferred compounds include: p-sec butylphenyl chlorosulfate, p-t-butylphenyl chlorosulfate, p-t-amyphenyl chlorosulfate, p-t-cumylphenyl chlorosulfate, 4-t-pentylphenyl chlorosulfate, 4-octylphenyl chlorosulfate, 4-pentylphenyl acid sulfate, octyl acid sulfate, bispenyl diacid sulfate, zosteric acid, p-sulfoxy cinnamic acid, p-sulfoxy ferulic acid, m,p-disulfoxy caffeic acid, benzoic sulfate, vanillic acid, gentissic acid sulfate, gallic acid sulfate and protochateuic acid, and the salts of the aforesaid acids.

Other features and advantages of the invention will be apparent from the following detailed description and claims.

DETAILED DESCRIPTION OF THE INVENTION

General

Figure 1:
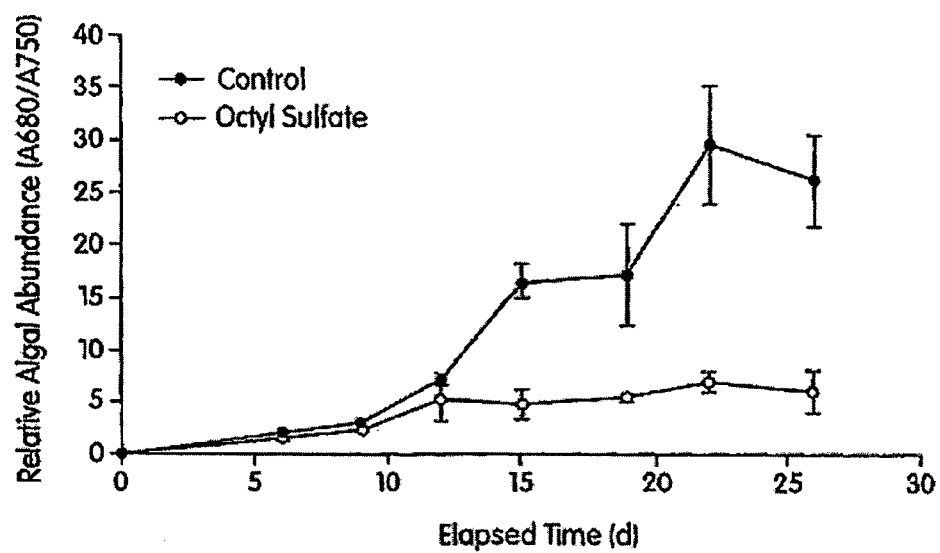
FIG. 1 is a diagrammatic representation of the results of marine algae attachment assays measuring the abundance of algal biofilm development on the inert coating RTV-11 compared to biofilm development on RTV-11 with octyl sulfate incorporated into the coating. Relative algal abundance represents the attachment of the marine algae to the tested surface. Error bars indicate 1 standard error of the mean (n=3) for each treatment. The ratio of the optical densities measured at wavelengths 680 nm and 750 nm ($A_{680}/A_{750}$) at time O was used as a baseline reference for all samples.

In general, the present invention relates to the prevention of accumulation of microorganisms on any surface wherein such accumulation has a deleterious effect on human or animal health. In particular, the present invention relates to the prevention of those conditions affecting human or animal health that involve fouling. Fouling events involve recognition between a biologic and a surface, adhesion of the biologic to the surface, and the subsequent activity of the biologic. As understood herein, the formation of a biofilm is a type of fouling. Biofilms with health effects commonly contain infectious microorganisms.

In a health-related environment, fouling can result in biofilm formation. Biofilm formation is understood to cause local contamination of an affected area with potential for invasive local infection and for systemic infection. Microorganisms may damage tissues in three ways: 1) they can enter or contact host cells and directly cause cell death; 2) they can release endotoxins or exotoxins that kill cells at a distance, release enzymes that degrade tissue components, or damage blood vessels and cause ischemic necrosis; and 3) they can induce host-cellular responses that, although directed against the invader, may cause additional tissue damage, including suppuration, scarring and hypersensitivity reactions. An infection, whether local or systemic, represents the penetration of microorganisms into a host with the production of tissue damage or the elicitation of host defense mechanisms or both, leading to clinically identifiable symptoms. Common local symptoms can include pain, tenderness, swelling and interference with function. Common systemic symptoms can include fever, malaise and hyperdynamic cardiovascular effects. Massive bloodstream invasion by infectious agents can rapidly become fatal.

When an infection has its origins in a biofilm surrounding an object in the body, whether a naturally occurring object or a foreign one, the infection often cannot be controlled without removing that object. If the object is naturally occurring, like devascularized or necrotic tissue, it is removed surgically via a process called debridement. If the object is a foreign one, such as a medical device, it is removed entirely. At times a rim of tissue must be removed along with the contaminated object to ensure maximal removal of contaminating material. If the material being removed is essential for health, a similar article may need to be replaced in the same location; the replacement article will be especially prone to infection because of the residual microorganisms in the area.

Definitions

For convenience, certain terms employed in the specification, examples, and appended claims are described below.

The term "acylamino" is art-recognized and refers to a moiety that can be represented by the general formula:

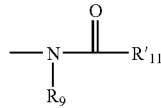

wherein $R_9$ is as defined below, and $R'_{11}$ represents a hydrogen, an alkyl, an alkenyl or —$(CH_2)_m$—$R_8$, where m and $R_8$ are as defined below.

The terms "alkenyl" and "alkynyl" refer to unsaturated aliphatic groups analogous in length and possible substitution to the alkyls described below, but that comprise a double or triple bond, respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described below.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3-10 carbon atoms in their ring structure, and more preferably have 5, 6 or 7 carbons in the ring structure.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined below. Representative alkylthio groups include methylthio, ethylthio, and the like.

The term "amido" is art recognized as an amino-substituted carbonyl and includes a moiety that can be represented by the general formula:

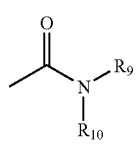

wherein $R_9$, $R_{10}$ are as defined below. Preferred embodiments of the amide will not include imides which may be unstable.

The terms "amine" and "amino" are art recognized and refer to both unsubstituted and substituted amines, e.g., a moiety that can be represented by the general formula:

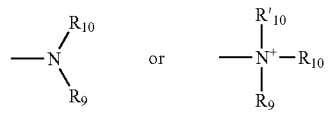

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "anti-fouling compound" as used herein refers those chemical formulations that impair, inhibit, prevent or retard biofouling. An anti-fouling ("AF") compound can be present in an acid form or as a salt thereof.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more rings in which two or more carbons are common to two adjoining rings (the rings are "fused") wherein at least one of the rings is aromatic, e.g., the other rings can be cycloalkyls, cycloalkenyls, cycloalkynyls, aryls and/or heterocyclyls.

The term "arylalkyl", as used herein, refers to an alkyl group substituted with an aryl group (e.g., an aromatic or heteroaromatic group).

The term "bioavailable" is meant to refer to an appropriate location, orientation or formulation of a compound for performance of the compound's bioactivity.

"Biofilm" refers to an accumulation of organisms on a surface. A mature biofilm can comprise a colony of microorganisms resident upon a surface surrounded by an exopolysaccharide.

"Biofilm resistant" or "antifouling" refers to inhibition or decrease in the amount of biofouling organisms that attach and/or grow.

A "biofoul or biofilm resistant coating" refers to any coating (as defined herein) that impairs, inhibits, prevents or retards the attachment and/or growth of biofouling organisms The term "carbocycle", as used herein, refers to an aromatic or non-aromatic ring in which each atom of the ring is carbon.

The term "carbonyl" is art recognized and includes such moieties as can be represented by the general formula:

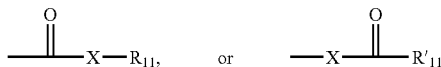

wherein X is a bond or represents an oxygen or a sulfur, and $R_{11}$ represents a hydrogen, an alkyl, an alkenyl, $—(CH_2)_m—R_8$ or a pharmaceutically acceptable salt, $R'_{11}$ represents a hydrogen, an alkyl, an alkenyl or $—(CH_2)_m—R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

"Contacting" as used herein refers to any means for providing the compounds of the invention to a surface to be protected from biofouling. Contacting can include spraying, wetting, immersing, dipping, painting, bonding or adhering or otherwise providing a surface with a compound of the invention.

A "coating" refers to any temporary, semipermanent or permanent layer, covering or surface. A coating can be a gas, vapor, liquid, paste, semi-solid or solid. In addition a coating can be applied as a liquid and solidify into a hard coating. Examples of coatings include polishes, surface cleaners, caulks, adhesives, finishes, paints, waxes polymerizable compositions (including phenolic resins, silicone polymers, chlorinated rubbers, coal tar and epoxy combinations, epoxy resin, polyamide resins, vinyl resins, elastomers, acrylate polymers, fluoropolymers, polyesters and polyurethanes, latex). Silicone resins, silicone polymers (e.g. RTV polymers) and silicone heat cured rubbers are suitable coatings for use in the invention and described for example in the Encyclopedia of Polymer Science and Engineering (1989) 15: 204 et seq. Coatings can be ablative or dissolvable, so that the dissolution rate of the matrix controls the rate at which AF agents are delivered to the surface. Coatings can also be non-ablative, and rely on diffusion principles to deliver an AF agent to the surface. Non-ablative coatings can be porous or non-porous. A coating containing an AF agent freely dispersed in a polymer binder is referred to as "monolithic" coating. Elasticity can be engineered into coatings to accommodate pliability, e.g. swelling or shrinkage, of the surface to be coated.

A "component" is a part of an apparatus that is structurally integrated with that apparatus. A component may be applied to a surface of an apparatus, contained within the substance of the apparatus, retained in the interior of the apparatus, or any other arrangement whereby that part is an integral element of the structure of the apparatus. As an example, the silicone covering surrounding the mechanical part of a pacemaker is a component of the pacemaker. A component may be the lumen of an apparatus where the lumen performs some function essential to the overall function of the apparatus. The lumen of a tissue expander port is a component of the tissue expander. A component can refer to a reservoir or a discrete area within the apparatus specifically adapted for the delivery of a fluid to a surface of the apparatus. A reservoir within an implantable drug delivery device is a component of that device.

A "delivery system" refers to any system or apparatus or component whereby the disclosed antifouling compounds can be delivered to a surface upon which biofilm formation is to be inhibited. Representative delivery systems can include encapsulation of the agent, incorporation of the agent in the substance of an article of manufacture, or inserting the agent into the matrices or pores of a suitable object, so that the agent is able to reach the targeted surface in sufficient amount to inhibit biofilm. A delivery system can comprise a coating. A delivery system can comprise a mechanical object adapted for the delivery of the antifouling compound to a surface. Other mechanisms comprising delivery systems will be apparent to those of skill in the relevant arts.

"Dressing" refers to any bandage or covering applied to a lesion or otherwise used to prevent or treat infection. Examples include wound dressings for chronic wounds (such as pressure sores, venous stasis ulcers and burns) or acute wounds and dressings over percutaneous devices such as IVs or subclavian lines intended to decrease the risk of line sepsis due to microbial invasion. For example, the compositions of the invention could be applied at the percutaneous puncture site, or could be incorporated in the adherent dressing material applied directly over the entry site.

The phrase "effective amount" refers to an amount of the disclosed antifouling compounds that significantly reduces the number of organisms that attach to a defined surface (cells/mm$^2$) relative to the number that attach to an untreated surface. Particularly preferred are amounts that reduce the number of organisms that attach to the surface by a factor of at least 2. Even more preferred are amounts that reduce the surface attachment of organisms by a factor of 4, more preferably by a factor of 6. An effective amount of the disclosed antifouling compound is said to inhibit the formation of biofilms, and to inhibit the growth of organisms on a defined surface. The term "inhibit," as applied to the effect of an antifouling compound on a surface includes any action that significantly reduces the number of organisms that attach thereto.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, *Advanced Organic Chemistry*, McGraw Hill Book Company, New York, (1977 edition) pp. 251–259. The Hammett constant values are generally negative for electron donating groups (σ[P]=−0.66 for $NH_2$) and positive for electron withdrawing groups (σ[P]=0.78 for a nitro group), σ[P] indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

A "graft" refers to a living tissue (e.g. skin, bone) that is introduced into an anatomic site in a patient's body. As understood herein, the term "graft" does not refer to those transplanted organs or tissues that are surgically connected to a macroscopic blood supply, such as a transplanted kidney or a microsurgically vascularized fibula. Since grafts, as understood herein, are devascularized when they are moved, they are abnormally susceptible to infection. As grafts heal, they acquire a blood supply and are restored to normal immune status. A graft may be derived from the host, and is termed an autograft. A graft may be derived from a donor of the same species or from another species; such grafts are termed allografts and xenografts respectively.

The term "health-related environment" is understood to include all those environments where activities are carried out that are implicated in the restoration or maintenance of human health. A health-related environment can be a medical environment, where activities are carried out directly or indirectly intended to restore human health. An operating room, a doctor's office, a hospital room, and a factory making medical equipment are all examples of medical environments. Other health-related environments can include industrial or residential sites where activities pertaining to human health are carried out. Such activities include food processing, water purification, and sanitation.

The term "half-life" refers to the amount of time required for half of a compound to be eliminated or degraded by natural processes.

The term "heteroatom" as used herein means an atom of any element other than carbon or hydrogen. Preferred heteroatoms are nitrogen, oxygen, sulfur and phosphorous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

An "implant" is any object intended for placement in a human body that is not a living tissue. Implants include naturally derived objects that have been processed so that their living tissues have been devitalized. As an example, bone grafts can be processed so that their living cells are removed, but so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components. The term "implant" can be applied to the entire spectrum of medical devices intended for placement in a human body.

The terms "infectious microorganisms" or "infectious agents" as used herein refers to disease causing or contributing bacteria (including gram-negative and gram-positive organisms, such as *Staphylococci* sps. (e.g. *Staphylococcus aureus*, *Staphylococcus epidermis*), *Enterococcus* sp. (*E. faecalis*), *Pseudomonas* sp. (*P. aeruginosa*), *Escherichia* sp. (*E. coli*), *Proteus* sp. (*P. mirabilis*)), fungi (including *Candida albicans*), viruses and protists.

"Medical device" refers to a non-naturally occurring object that is inserted or implanted in a subject or applied to a surface of a subject. Medical devices can be made of a variety of biocompatible materials, including: metals, ceramics, polymers, gels and fluids not normally found within the human body. Examples of polymers useful in fabricating medical devices include such polymers as silicones, rubbers, latex, plastics, polyanhydrides, polyesters, polyorthoesters, polyamides, polyacrylonitrile, polyurethanes, polyethylene, polytetrafluoroethylene, polyethylenetetraphthalate and polyphazenes. Medical devices can also be fabricated using certain naturally-occurring materials or treated naturally-occurring materials. As an example, a heart valve can be fabricated by combining a treated porcine heart valve with an affixation apparatus using artificial materials. Medical devices can include any combination of artificial materials, combinations selected because of the particular characteristics of the components. For example, a hip implant can include a combination of a metallic shaft to bear the weight, a ceramic artificial joint and a polymeric glue to affix the structure to the surrounding bone. An implantable device is one intended to be completely imbedded in the body without any structure left outside the body (e.g. heart valve). An insertable device is one that is partially imbedded in the body but has a part intended to be external (e.g. a catheter or a drain). Medical devices can be intended for short-term or long-term residence where they are positioned. A hip implant is intended for several decades of use, for example. By contrast, a tissue expander may only be needed for a few months, and is removed thereafter. Insertable devices tend to remain in place for shorter times than implantable devices, in part because they come into more contact with microorganisms that can colonize them.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —SO$_2$—.

The terms ortho, meta and para apply to 1,2-, 1,3- and 1,4-disubstituted benzenes, respectively. For example, the names 1,2-dimethylbenzene and ortho-dimethylbenzene are synonymous.

A "pharmaceutically effective amount" refers to an appropriate amount to obtain a therapeutic effect. Toxicity and therapeutic efficacy of compounds can be determined by standard pharmaceutical procedures in cell cultures or experimental animals, e.g., for determining The Ld$_{50}$ (The Dose Lethal To 50% Of The Population) And The Ed$_{50}$ (the dose therapeutically effective in 50% of the population). The dose ratio between toxic and therapeutic effects is the therapeutic index and it can be expressed as the ratio LD$_{50}$/ED$_{50}$. Compounds which exhibit large therapeutic indices are preferred. The effective amount may vary within a range depending upon the dosage form employed and the route of administration utilized. A dose may be formulated in animal models to achieve a circulating plasma concentration range that includes the IC$_{50}$ (i.e., the concentration of the test compound which achieves a half-maximal inhibition of symptoms) as determined in cell culture.

"Pharmaceutical effective carrier" refers to a physiologically acceptable carrier or excipient. Thus, the compounds and their physiologically acceptable salts and solvates may be formulated for administration by, for example, injection, inhalation or insufflation (either through the mouth or the nose) or oral, buccal, parenteral or rectal administration. For therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included. For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration-may be through nasal sprays or using suppositories. For topical administration, the oligomers of the invention are formulated into ointments, salves, gels, or creams as generally known in the art. A wash solution can be used locally to treat an injury or inflammation to accelerate healing.

A "phosphoryl" can in general be represented by the formula:

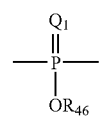

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

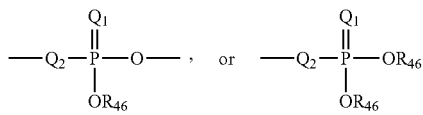

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "polar, aprotic solvent" means a polar solvent as defined above which has no available hydrogens to exchange with the compounds of this invention during reaction, for example DMF, acetonitrile, diglyme, DMSO, or THF.

A "polar solvent" means a solvent which has a dielectric constant ($\in$) of 2.9 or greater, such as DMF, THF, ethylene glycol dimethyl ether (DME), DMSO, acetone, acetonitrile, methanol, ethanol, isopropanol, n-propanol, t-butanol or 2-methoxyethyl ether. Preferred solvents are DMF, DME, NMP, and acetonitrile.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

"Release rate" or "flux" refers to the rate of delivery or diffusion of a compound to or from a surface. The release rate may be constant or sustained over a period of time or may be variable. However, constant, controlled or sustained release rates are generally preferred. Steady state or sustained release may be effected by use of a reservoir membrane (i.e. a two layer coating in which one layer contains the active agent and the other creates a membrane through which the active agent can be released). The active agent could alternatively be microencapsulated within any of a variety of matrices for sustained release. Preferred release rates for applications that require a short duration of AF activity or that are frequently applied are more than about 100 $\mu gcm^{-2}d^{-1}$. Preferred release rates for sustained release are typically less than 100 $\mu gcm^{-2}d^{-1}$, more preferably less than about 75, 50, 25, 20, 15, 10 or 5 $\mu gcm^{-2}d^{-1}$.

The term "soluble" refers to the ability to be loosened or dissolved.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfate" is art recognized and includes a moiety that can be represented by the general formula:

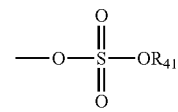

in which $R_{41}$ is as defined below.

A "sulfate binding moiety" refers to a moiety that is capable of binding or otherwise associating with a sulfate or sulfonate group.

The term "sulfonate" is art recognized and includes a moiety that can be represented by the general formula:

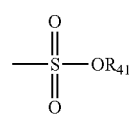

in which $R_{41}$ is an electron pair, hydrogen, alkyl, cycloalkyl, or aryl.

The terms "sulfoxido" or "sulfinyl", as used herein, refers to a moiety that can be represented by the general formula:

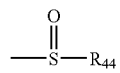

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "surface", as used herein, refers to any surface whether in an industrial or a medical setting, that provides an interface between an object and a fluid, permitting at least intermittent contact between the object and the fluid. A surface, as understood herein, further provides a plane whose mechanical structure, without further treatment, is compatible with the adherence of microorganisms. Surfaces compatible with biofilm formation may be smooth or irregular. Fluids contacting the surfaces can be stagnant or flowing, and can flow intermittently or continuously, with laminar or turbulent or mixed rheologies. A surface upon which a biofilm forms can be dry at times with sporadic fluid contact, or can have any degree of fluid exposure including total immersion. Fluid contact with the surface can take place via aerosols or other means for air-borne fluid transmission.

Biofilm formation with health implications can involve those surfaces in all health-related environments, including surfaces found in medical environments and those surfaces in industrial or residential environments that are involved in those functions essential to well-being like nutrition, sanitation and the prevention of disease.

A surface of an article adapted for use in a medical environment can be capable of sterilization using autoclaving, biocide exposure, irradiation or gassing techniques like ethylene oxide exposure. Surfaces found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts.

Surfaces found in the medical environment include also the inner and outer aspects of pieces of medical equipment, medical gear worn or carried by personnel in the health care setting. Such surfaces can include counter tops and fixtures in areas used for medical procedures or for preparing medical apparatus, tubes and canisters used in respiratory treatments, including the administration of oxygen, of solubilized drugs in nebulizers and of anesthetic agents. Also included are those surfaces intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

Surfaces in contact with liquids are particularly prone to biofilm formation. As an example, those reservoirs and tubes used for delivering humidified oxygen to patients can bear biofilms inhabited by infectious agents. Dental unit waterlines similarly can bear biofilms on their surfaces, providing a reservoir for continuing contamination of the system of flowing and aerosolized water used in dentistry.

Sprays, aerosols and nebulizers are highly effective in disseminating biofilm fragments to a potential host or to another environmental site. It is understood to be especially important to health to prevent biofilm formation on those surfaces from whence biofilm fragments can be carried away by sprays, aerosols or nebulizers contacting the surface.

Other surfaces related to health include the inner and outer aspects of those articles involved in water purification, water storage and water delivery, and those articles involved in food processing. Surfaces related to health can also include the inner and outer aspects of those household articles involved in providing for nutrition, sanitation or disease prevention. Examples can include food processing equipment for home use, materials for infant care, tampons and toilet bowls.

"Sustained release" or "controlled release refers to a relatively constant or prolonged release of a compound of the invention from a surface. This can be accomplished through the use of diffusional systems, including reservoir devices in which a core of a compound of the invention is surrounded by a porous membrane or layer, and also matrix devices in which the compound is distributed throughout an inert matrix. Materials which may be used to form reservoirs or matrices include silicones, acrylates, methacrylates, vinyl compounds such as polyvinyl chloride, olefins such as polyethylene or polypropylene, fluoropolymers such as polytetrafluorethylene, and polyesters such as terephthalates. The diffusional systems may be molded into a film or other layer material which is then placed in adherent contact with the structure intended for underwater use. Alternatively, the compounds of the invention may be mixed with a resin, e.g., polyvinyl chloride and then molded into a formed article, which integrally incorporates the compound to form a structure having a porous matrix which allows diffusion of the compound, or a functional portion thereof, into the surrounding environment. Microencapsulation techniques can also be used to maintain a sustained focal release of a compound of the invention. Microencapsulation may also be used for providing improved stability. The encapsulated product can take the form of, for example, spheres, aggregates of core material embedded in a continuum of wall material, or capillary designs. The core material of a microcapsule containing a sulfate ester AF agent may be in the form of a liquid droplet, an emulsion, a suspension of solids, a solid particle, or a crystal. The skilled artisan will be aware of numerous materials suitable for use as microcapsule coating materials, including, but not limited to, organic polymers, hydrocolloids, lipids, fats, carbohydrates, waxes, metals, and inorganic oxides. Silicone polymers are the most preferred microcapsule coating material for treatment of surfaces. Microencapsulation techniques are well known in the art and are described in the Encyclopedia of Polymer Science and Engineering, Vol. 9, pp. 724 et seq. (1989) hereby incorporated by reference.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Compositions of the Invention

In certain embodiments, the compositions of the present invention comprise an anti-fouling compound represented by general structure 1:

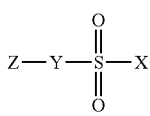

wherein
X represents —OH, —O(aryl), —O(acyl), —O(sulfonyl), —CN, F, Cl, or Br;
Y represents O, S, Se, or NR;
Z represents optionally substituted alkyl, heteroalkyl, cycloalkyl, heterocycloalkyl, aryl, heteroaryl, aralkyl, heteroaralkyl, or —(CH$_2$)$_m$—R$_{80}$;
R represents independently for each occurrence hydrogen, alkyl, heteroalkyl, aryl, heteroaryl, aralkyl, heteroaralkyl, or —(CH$_2$)$_m$—R$_{80}$;
R$_{80}$ represents independently for each occurrence aryl, cycloalkyl, cycloalkenyl, heterocyclyl, or polycyclyl; and
m is an integer in the range 0 to 8 inclusive.

Particularly stable compounds are represented by general structure 1 and the attendant definitions, wherein X represents —OH, F, Cl, or Br.

In other preferred embodiments, the compositions of the present invention comprise an anti-fouling compound represented by general structure 1 and the attendant definitions, wherein Y represents O.

In certain embodiments, the compositions of the present invention comprise an anti-fouling compound represented by general structure 1 and the attendant definitions, wherein Z represents optionally substituted alkyl, aryl, or —(CH$_2$)$_m$—R$_{80}$.

In certain embodiments, the compositions of the present invention comprise an anti-fouling compound represented by general structure 1 and the attendant definitions, wherein Z represents optionally substituted alkylphenyl, heteroalkylphenyl, arylphenyl, or heteroarylphenyl.

In certain embodiments, the compositions of the present invention comprise an anti-fouling compound represented by general structure 1 and the attendant definitions, wherein Z represents 4-(2-methylpropyl)phenyl, 4-(1,1-dimethylethyl)phenyl, 4-(1,1-dimethylpropyl)phenyl, 4-pentylphenyl, 4-(1-methyl-1-phenylethyl)phenyl, or 4-(1-methylheptyl)phenyl.

In certain embodiments, the compositions of the present invention comprise an anti-fouling compound represented by general structure 1 and the attendant definitions, wherein R represents H or alkyl.

In certain embodiments, the compositions of the present invention comprise an anti-fouling compound represented by general structure 1 and the attendant definitions, wherein X represents —OH, F, Cl, or Br; and Y represents O.

In certain embodiments, the compositions of the present invention comprise an anti-fouling compound represented by general structure 1 and the attendant definitions, wherein X represents —OH or Cl; and Y represents O.

In certain embodiments, the compositions of the present invention comprise an anti-fouling compound represented by general structure 1 and the attendant definitions, wherein X represents —OH, F, Cl, or Br; and Z represents optionally substituted alkyl, aryl, or —(CH$_2$)$_m$—R$_{80}$.

In certain embodiments, the compositions of the present invention comprise an anti-fouling compound represented by general structure 1 and the attendant definitions, wherein X represents —OH or Cl; and Z represents optionally substituted alkyl, aryl, or —(CH$_2$)$_m$—R$_{80}$.

In certain embodiments, the compositions of the present invention comprise an anti-fouling compound represented by general structure 1 and the attendant definitions, wherein X represents —OH, F, Cl, or Br; and Z represents optionally substituted alkylphenyl, heteroalkylphenyl, arylphenyl, or heteroarylphenyl.

In certain embodiments, the compositions of the present invention comprise an anti-fouling compound represented by general structure 1 and the attendant definitions, wherein X represents —OH or Cl; and Z represents optionally substituted alkylphenyl, heteroalkylphenyl, arylphenyl, or heteroarylphenyl.

In certain embodiments, the compositions of the present invention comprise an anti-fouling compound represented by general structure 1 and the attendant definitions, wherein X represents —OH, F, Cl, or Br; and Z represents 4-(2-methylpropyl)phenyl, 4-(1,1-dimethylethyl)phenyl, 4-(1,1-dimethylpropyl)phenyl, 4-pentylphenyl, 4-(1-methyl-1-phenylethyl)phenyl, or 4-(1-methylheptyl)phenyl.

In certain embodiments, the compositions of the present invention comprise an anti-fouling compound represented by general structure 1 and the attendant definitions, wherein X represents —OH or Cl; and Z represents 4-(2-methylpropyl)phenyl, 4-(1,1-dimethylethyl)phenyl, 4-(1,1-dimethylpropyl)phenyl, 4-pentylphenyl, 4-(1-methyl-1-phenylethyl)phenyl, or 4-(1-methylheptyl)phenyl.

In certain embodiments, the compositions of the present invention comprise an anti-fouling compound represented by general structure 1 and the attendant definitions, wherein Y represents O; and Z represents optionally substituted alkyl, aryl, or —(CH$_2$)$_m$—R$_{80}$.

In certain embodiments, the compositions of the present invention comprise an anti-fouling compound represented by general structure 1 and the attendant definitions, wherein Y represents O; and Z represents optionally substituted alkylphenyl, heteroalkylphenyl, arylphenyl, or heteroarylphenyl.

In certain embodiments, the compositions of the present invention comprise an anti-fouling compound represented by general structure 1 and the attendant definitions, wherein Y represents O; and Z represents 4-(2-methylpropyl)phenyl, 4-(1,1-dimethylethyl)phenyl, 4-(1,1-dimethylpropyl)phenyl, 4-pentylphenyl, 4-(1-methyl-1-phenylethyl)phenyl, or 4-(1-methylheptyl)phenyl.

In certain embodiments, the compositions of the present invention comprise an anti-fouling compound represented by general structure 1 and the attendant definitions, wherein X represents —OH, F, Cl, or Br; Y represents O; and Z represents optionally substituted alkyl, aryl, or —$(CH_2)_m$—$R_{80}$.

In certain embodiments, the compositions of the present invention comprise an anti-fouling compound represented by general structure 1 and the attendant definitions, wherein X represents —OH or Cl; Y represents O; and Z represents optionally substituted alkyl, aryl, or —$(CH_2)_m$—$R_{80}$.

In certain embodiments, the compositions of the present invention comprise an anti-fouling compound represented by general structure 1 and the attendant definitions, wherein X represents —OH, F, Cl, or Br; Y represents O; and Z represents optionally substituted alkylphenyl, heteroalkylphenyl, arylphenyl, or heteroarylphenyl.

In certain embodiments, the compositions of the present invention comprise an anti-fouling compound represented by general structure 1 and the attendant definitions, wherein X represents —OH or Cl; Y represents O; and Z represents optionally substituted alkylphenyl, heteroalkylphenyl, arylphenyl, or heteroarylphenyl.

In certain embodiments, the compositions of the present invention comprise an anti-fouling compound represented by general structure 1 and the attendant definitions, wherein X represents —OH, F, Cl, or Br; Y represents O; and Z represents 4-(2-methylpropyl)phenyl, 4-(1,1-dimethylethyl) phenyl, 4-(1,1-dimethylpropyl)phenyl, 4-pentylphenyl, 4-(1-methyl-1-phenylethyl)phenyl, or 4-(1-methylheptyl) phenyl.

In certain embodiments, the compositions of the present invention comprise an anti-fouling compound represented by general structure 1 and the attendant definitions, wherein X represents —OH or Cl; Y represents O; and Z represents 4-(2-methylpropyl)phenyl, 4-(1,1-dimethylethyl)phenyl, 4-(1,1-dimethylpropyl)phenyl, 4-pentylphenyl, 4-(1-methyl-1-phenylethyl)phenyl, or 4-(1-methylheptyl)phenyl.

One of skill in the art will recognize that the composition of the invention can be varied as required to optimize the overall chemical properties of the particular compound for specific uses, while retaining the AF activity. For example, the length of an alkyl chain can be extended or shortened to control the rate of dissolution of the compound from a structure or a coating. Alternatively, additional functional groups can be added to the alkyl chain to further vary the chemical nature of the molecule.

Specific Utilities

Anticoagulant Activity

As shown in the following examples, compounds of the invention have been found to possess certain anti-coagulation activities, such as possessed by the sulfated mucopolysaccharide heparin. Heparin is believed to inhibit the clotting cascade by binding to, and thereby activating, antithrombin III, a plasma protein that inactivates thrombin by forming an irreversible complex with it. This complex is similar to the acyl-enzyme complex formed between trypsin and pancreatic trypsin inhibitor. Heparin is produced by mast cells near the walls of blood vessels and acts as an anticoagulant by increasing the rate of formation of the irreversible complex between thrombin and antithrombin III. Antithrombin III also inhibits other proteolytic components of the clotting cascade, such as Factors $IX_a$, $X_a$, and $XI_a$.

The activity for the low molecular weight zosteric acid molecule has been observed to be considerably less than that observed for heparin. Heparin was effective at preventing clot formation at concentrations well below 0.1 mg/ml, while zosteric acid was effective only at concentrations exceeding 10 mg/ml. However, the effectiveness of heparin-like anticoagulants is strongly linked to size, with high molecular weight molecules being more effective. Therefore certain of the higher molecular weight compounds of the invention should prove more effective.

Heparin has been used extensively for prophylaxis and treatment of deep vein thrombosis. However, heparin has several limitations. For example, heparin, a relatively large molecule, has shown limited efficacy in inhibiting thrombin activity incorporated into a fibrin clot. In addition, heparin has a short intravenous half-life. Therefore, in certain applications, the use of compounds of the invention can be advantageous in performing certain anti-clotting prophylaxis or therapies. The compounds of the invention can also be formulated as covalent derivatized for the treatment and prevention of clotting conditions. For example, a covalent antithrombin-heparin complex has proven to be more effective in reducing clot weight in vivo than thrombin and heparin combination therapy. Accordingly, the invention provides methods and reagents for creating derivatized components of the fibrin clotting cascade, including antithrombin.

The compounds of the invention can potentially be orally delivered, whereas heparin must be delivered intravenously. In addition, the heparin-like property of the compounds of the invention render them particularly suitable for incorporating into medical materials where an anti-coagulant effect is desired.

Contraceptive Activity

As shown in the following examples, compounds of the invention have been found to inhibit fertilization. As a result, the compounds of the invention can be used as contraceptives. Contraceptives comprised of the instant claimed compounds can be formulated as either routinely reapplied coatings, described above, foams, jellies and suppositories, or alternatively as semi-permanent coatings to be used on prophylactic articles of manufacture, (e.g., condoms or diaphragms). Alternatively, sulfate esters can be formulated as incorporations into such articles during manufacture.

Biofilm Inhibitory Activities

By interfering with the attachment of organisms to surfaces, the instant claimed compounds have broad applicability in effectively inhibiting the development of biofilms on medical and health related surfaces.

For example, wounds where skin grafts or skin substitutes such as cultured epidermal cells have been applied are particularly vulnerable to invasion by ambient infectious organisms. These wound covers have no intrinsic blood supply, so are unable to fight off infection. When certain organisms invade a skin graft site, they destroy the skin graft entirely. Infectious organisms can similarly invade a wound where part of the skin has been removed, either through trauma or as part of a treatment; local infection of such a partial-thickness wound can kill the skin entirely and prevent it from healing or regenerating. In this context, a wound able to heal itself has been converted to one that will heal extremely slowly if at all, likely requiring a skin graft for closure. These wounds are particularly adapted for the application of an AF agent that will reduce the tendency for infectious organisms to accumulate without impacting the general healing process. Formulation of such a preparation is consistent with the skill of ordinary practitioner in these arts.

Vehicles comprised of claimed compounds of the invention adapted for skin or tissue application can include materials for temporary application, or those materials that are more durable, forming films or semi-permanent coatings like paints. Creams and ointments can be formed that are occlusive or that are semi-permeable.

Compounds of the invention can be formulated as a solution suitable for applying to skin surfaces that will form a durable film that can remain in place over a sustained period of time. Such a solution could be applied to the hands of medical personnel underneath surgical gloves to reduce the contamination hazards from glove tears. Such a solution could also be applied to exposed skin surfaces, for example the uncovered face, of medical personnel in settings where contaminated splashes are likely. This embodiment would be useful for personnel like emergency medical technicians and emergency room doctors and nurses. A vehicle for applying compounds of the invention like a lotion or a cream would protect exposed surfaces of those personnel, and reduce the risk and the fear of possible infection from topical exposures to contaminated fluids.

For household use, compounds of the invention can be incorporated into ointments to protect injured areas and to protect intact skin from prolonged microbial exposure. As an example, a topical compound of the invention can inhibit the development of fungal infections like athlete's foot; the agent can be dispensed as a cream, an ointment, a powder or a spray. Other preparations can be used in moist areas to inhibit local yeast infections. Preparations adapted for intravaginal use can provide prophylaxis against *Candida vaginitis* in patients taking broad-spectrum antibiotics, where alteration of the normal balance of flora can result in *Candida* overgrowth and subsequent symptomatology. Applying a compound of the invention to the materials used for fabricating menstrual tampons may inhibit the formation of those Staph. species responsible for toxic shock syndrome.

The non-toxic nature of the compounds of the invention makes them suitable for direct application to living tissues. A liquid preparation may be applied to autogenous skin or bone grafts to protect these temporarily avascular tissues from microbial colonization and biofilm formation. The vehicle bearing the compound need only remain present and biologically active for a short period of time, because the grafted tissues will soon begin to acquire a blood supply, therewith acquiring more normal local immune responsiveness.

Any object placed in the body from outside it is susceptible to biological contamination with microorganisms and subsequent biofilm formation. Therefore, compounds according to the present invention can prevent such objects from becoming contaminated with microorganisms in the first place. Further, these technologies can be used to produce natural and synthetic materials resistant to contamination that are especially suited for replacing those objects that have already sustained infection, or that are intended for being placed in those anatomic sites where infections can be particularly devastating.

Naturally derived processed materials commonly are positioned in the body in order to provide a structure for ingrowth of the patient's own tissues. Examples include demineralized bone materials and hydroxyapatite. These materials are destined to be infiltrated or replaced entirely by the patient's tissue, during which time the exogenous material retains the desired shape or structural support in the affected area. These materials themselves are non-living and avascular. Colonization of these materials with microorganisms and biofilm formation can require their removal. If the material is removed, the shape or the structure that it is maintaining is destroyed and the progress made by tissue ingrowth is in vain. Application of compounds of the invention to these materials can enhance their resistance to biofilm formation and its consequences.

Certain naturally derived processed materials will be determined by artisans in these fields to be especially suitable for the application or incorporation of compounds of the invention. A material can be contacted with the claimed compounds in a variety of ways including immersion and coating. In forms where the material has interstices, an AF compound can reside therein as a liquid or as a gel. Fibrillar preparations can permit the fibers to be coated with the compound. Solid articles such as reconstructive blocks of hydroxyapatite can be painted with a coating of the compound for additional protection. These temporary means of application are appropriate for these materials because they only reside in the body temporarily, to be resorbed or replaced.

Implantable medical devices, using artificial materials alone or in combination with naturally-derived materials, can be treated with compounds either by surface coating or by incorporation. Metals may be suitably treated with surface coats while retaining their biological properties. In certain embodiments of the present invention, metals may be treated with paints or with adherent layers of polymers or ceramics that incorporate the compounds of the invention. Certain embodiments treated in this manner may be suitable for orthopedic applications, for example, pins, screws, plates or parts of artificial joints. Methods for surface treatment of metals for biological use are well-known in the relevant arts. Other materials besides metals can be treated with surface coats of compounds according to the present invention as the medical application requires.

Implantable devices may comprise materials suitable for the incorporation of the instant claimed compounds. Embodiments whose components incorporate compounds of the invention can include polymers, ceramics and other substances. Materials fabricated from artificial materials can also be destined for resorption when they are placed in the body. Such materials can be called bioabsorbable. As an example, polyglycolic acid polymers can be used to fabricate sutures and orthopedic devices. Those of ordinary skill in these arts will be familiar with techniques for incorporating agents into the polymers used to shape formed articles for medical applications. AF agents can also be incorporated into glues, cements or adhesives, or in other materials used to fix structures within the body or to adhere implants to a body structure. Examples include polymethylmethacrylate and its related compounds, used for the affixation of orthopedic and dental prostheses within the body. The presence of the compounds of the instant invention can decrease biofilm formation in those structures in contact with the glue, cement, or adhesive. Alternatively, a compound of the invention can coat or can permeate the formed article. In these compositions, the formed article allows diffusion of the compound, or functional portion thereof, into the surrounding environment, thereby preventing fouling of the appliance itself. Microcapsules bearing compounds can also be imbedded in the material. Materials incorporating compounds are adaptable to the manufacture of a wide range of medical devices, some of which are disclosed below. Other examples will be readily apparent to those practitioners of ordinary skill in the art.

In one embodiment, compounds of the invention can be applied to or incorporated in certain medical devices that are intended to be left in position permanently to replace or restore vital functions. As one example, ventriculoatrial or ventriculoperitoneal shunts are devised to prevent cerebrospinal fluid from collecting in the brain of patients whose normal drainage channels are impaired. As long as the shunt functions, fluid is prevented from accumulating in the brain and normal brain function can continue. If the shunt ceases to function, fluid accumulates and compresses the brain, with potentially life-threatening effect. If the shunt becomes infected, it causes an infection to enter the central portions of the brain, another life-threatening complication. These shunts commonly include a silicone elastomer or another polymer as part of their fabrication. Silicones are understood to be especially suited for combination with compounds according to the present invention.

Another shunt that has life-saving import is a dialysis shunt, a piece of polymeric tubing connecting an artery and a vein in the forearm to provide the kidney failure patient a means by which the dialysis equipment can cleanse the bloodstream. Even though this is a high-flow conduit, it is susceptible to the formation of biofilms and subsequent infection. If a shunt becomes infected, it requires removal and replacement. Since dialysis may be a lifelong process, and since there are a limited number of sites where shunts can be applied, it is desirable to avoid having to remove one through infectious complications. Imbedding or otherwise contacting the compounds of the invention with the shunt material can have this desired effect.

Heart valves comprising artificial material are understood to be vulnerable to the dangerous complication of prosthetic valve endocarditis. Once established, it carries a mortality rate as high as 70%. Biofilms are integrally involved in the development of this condition. At present, the only treatment for established contamination is high-dose antibiotic therapy and surgical removal of the device. The contaminated valve must be immediately replaced, since the heart cannot function without it. Because the new valve is being inserted in a recently contaminated area, it is common for prosthetic valve endocarditis to affect the replacement valve as well. Artificial heart valves comprised of the compounds of the invention may reduce the incidence of primary and recurrent prosthetic valve endocarditis. Compounds of the invention can be applied to the synthetic portions or the naturally-derived portions of heart valves.

Pacemakers and artificial implantable defibrillators commonly comprise metallic parts in combination with other synthetic materials. These devices, which may be coated with a polymeric substance such as silicone are typically implanted in subcutaneous or intramuscular locations with wires or other electrical devices extending intrathoracically or intravascularly. If the device becomes colonized with microorganisms and infected, it must be removed. A new device can be replaced in a different location, although there are a finite number of appropriate implantation sites on the body. Devices comprising the compounds of the invention may inhibit contamination and infection, or substantially reduce the risk thereof.

Devices implanted into the body either temporarily or permanently to pump pharmacological agents into the body can comprise metallic parts in combination with other synthetic materials. Such devices, termed infusion pumps, can be entirely implanted or can be partially implanted. The device may be partially or entirely covered with a polymeric substance, and may comprise other polymers used as conduits or tubes. Incorporating AF agents according to the present invention into the coating materials imposed upon these devices or into the materials used for the devices themselves, their conduits or their tubing may inhibit their contamination and infection.

Equally lifesaving are the various vascular grafting prostheses and stents intended to bypass blocked arteries or substitute for damaged arteries. Vascular grafting prostheses, made of Teflon®, Dacron®, Gore-tex®, expanded polytetrafluoroethylene (e-PTFE), and related materials, are available for use on any major blood vessel in the body. Commonly, for example, vascular grafting prostheses are used to bypass vessels in the leg and are used to substitute for a damaged aorta. They are put in place by being sewn into the end or the side of a normal blood vessel upstream and downstream of the area to be bypassed or replaced, so that blood flows from a normal area into the vascular grafting prosthesis to be delivered to other normal blood vessels. Stents comprising metallic frames covered with vascular grafting prosthesis fabric are also available for endovascular application, to repair damaged blood vessels.

When a vascular grafting prosthesis becomes infected, it can spread infection through the entire bloodstream. Furthermore, the infection can weaken the attachment of the vascular grafting prosthesis to the normal blood vessel upstream or downstream, so that blood can leak out of it. If the attachment ruptures, there can be life-threatening hemorrhage. When a vascular grafting prosthesis becomes infected, it needs to be removed. It is especially dangerous to put another vascular grafting prosthesis in the same spot because of the risk of another infection, but there are often few other options. Vascular grafting prostheses comprising compounds of the invention can resist infections, thereby avoiding these devastating complications.

Vascular grafting prostheses of small caliber are particularly prone to clotting. A vascular grafting prosthesis comprising a compound of the invention may not only prevent biofilm formation, but also inhibit clotting as described above, allowing a smaller diameter vascular grafting prosthesis to be more reliable. A common site for clotting is the junction point between the vascular grafting prosthesis and the normal vessel, called the anastomosis. Even if an artificial vascular grafting prosthesis is not used, anywhere that two vessels are joined or anywhere there is a suture line that penetrates a natural blood vessel, there is a potential for clotting to take place. A clot in a vessel can occlude the vessel entirely or only partially; in the latter case, blood clots can be swept downstream, damaging local tissues. Using suture comprised of the compounds of the invention may inhibit clotting at these various suture lines. The smaller the vessel, the more likely that a clot forming within it will lead to a total occlusion. This can have disastrous results: if the main vessel feeding a tissue or an organ becomes totally occluded, that structure loses its blood supply and can die. Microsurgery provides dramatic examples of the damage that can occur with anastomotic clotting. In microsurgery, typically only a single tiny vessel is feeding an entire tissue structure like a finger or a muscle. If the vessel clots off, the tissue structure can quickly die. Microsurgery typically involves vessels only one to four millimeters in diameter. It is understood that the sutures penetrating the vessel at the anastomosis are likely sites for clots to form. Microsurgical sutures comprising a compound of the invention would result in localized administration of an anticoagulant at the site most likely to be damaged by clotting.

Suture material used to anchor vascular grafting prostheses to normal blood vessels or to sew vessels or other structures together can also harbor infections. Sutures used for these purposes are commonly made of prolene, nylon or other monofilamentous nonabsorbable materials. An infection that begins at a suture line can extend to involve the vascular grafting prosthesis. Suture materials comprising a compound of the invention would have increased resistance to infection.

A suture comprising a compound of the invention would be useful in other areas besides the vasculature. Wound infections at surgical incisions may arise from microorganisms that lodge in suture materials placed at various levels to close the incision. General surgery uses both nonabsorbable and absorbable sutures. Materials for nonabsorbable sutures include prolene and nylon. Absorbable sutures include materials like treated catgut and polyglycolic acid. Absorbable sutures retain tensile strength for periods of time from days to months and are gradually resorbed by the body. Fabricating an absorbable or a nonabsorbable suture comprising a compound of the invention and which retains the handling and tensile characteristics of the material is within the skill of artisans in the field.

A general principle of surgery is that when a foreign object becomes infected, it most likely needs to be removed so that the infection can be controlled. So, for example, when sutures become infected, they may need to be surgically removed to allow the infection to be controlled. Any area where surgery is performed is susceptible to a wound infection. Wound infections can penetrate to deeper levels of the tissues to involve foreign material that has been used as part of the operation. As an example, hernias are commonly repaired by suturing a plastic screening material called mesh in the defect. A wound infection that extends to the area where the mesh has been placed can involve the mesh itself, requiring that the mesh be removed. Surgical meshes comprising a compound of the invention can have increased resistance to infection. Surgical meshes are made of substances like Gore-tex®, Teflon®, nylon and Marlex®. Surgical meshes are used to close deep wounds or to reinforce the enclosure of body cavities. Removing an infected mesh can leave an irreparable defect, with life-threatening consequences. Avoiding infection of these materials is of paramount importance in surgery. Materials used for meshes and related materials can be formulated to include the claimed compounds of the instant invention.

Materials similar to vascular grafting prostheses and surgical meshes are used in other sites in the body. Medical devices used in these locations similarly can benefit from the compounds of the invention; when these devices are located in the bloodstream, these agents' anticoagulant effects provide further benefit. Examples include hepatic shunts, vena caval filters and atrial septal defect patches, although other examples will be apparent to practitioners in these arts.

Certain implantable devices intended to restore structural stability to body parts can be advantageously treated with the instant claimed compounds. A few examples follow, and others will be readily identified by ordinary skilled artisans. Implantable devices, used to replace bones or joints or teeth, act as prostheses or substitutes for the normal structure present at that anatomic site. Metallics and ceramics are commonly used for orthopedic and dental prostheses. Implants may be anchored in place with cements like polymethylmethacrylate. Prosthetic joint surfaces can be fabricated from polymers such as silicones or teflon. Entire prosthetic joints for fingers, toes or wrists can be made from polymers.

Medical prostheses comprising compounds of the invention would be expected to have reduced contamination and subsequent local infection, thereby obviating or reducing the need to remove the implant with the attendant destruction of local tissues. Destruction of local tissues, especially bones and ligaments, can make the tissue bed less hospitable for supporting a replacement prosthesis. Furthermore, the presence of contaminating microorganisms in surrounding tissues makes recontamination of the replacement prosthesis easily possible. The effects of repeated contamination and infection of structural prosthetics is significant: major reconstructive surgery may be required to rehabilitate the area in the absence of the prosthesis, potentially including free bone transfers or joint fusions. Furthermore, there is no guarantee that these secondary reconstructive efforts will not meet with infectious complications as well. Major disability, with possible extremity amputation, is the outcome from contamination and infection of a structural prosthesis.

Certain implantable devices are intended to restore or enhance body contours for cosmetic or reconstructive applications. A well-known example of such a device is the breast implant, a gel or fluid containing sac made of a silicone elastomer. Other polymeric implants exist that are intended for permanent cosmetic or reconstructive uses. Solid silicone blocks or sheets can be inserted into contour defects. Other naturally occurring or synthetic biomaterials are available for similar applications. Craniofacial surgical reconstruction can involve implantable devices for restoring severely deformed facial contours in addition to the techniques used for restructuring natural bony contours. These devices, and other related devices well-known in the field, are suitable for coating with or impregnation with sulfate ester AF agents to reduce their risk of contamination, infection and subsequent removal.

Tissue expanders are sacs made of silicone elastomers adapted for gradual filling with a saline solution, whereby the filling process stretches the overlying tissues to generate an increased area of tissue that can be used for other reconstructive applications. Tissue expanders can be used, for example, to expand chest wall skin and muscle after mastectomy as a step towards breast reconstruction. Tissue expanders can also be used in reconstructing areas of significant skin loss in burn victims. A tissue expander is usually intended for temporary use: once the overlying tissues are adequately expanded, they are stretched to cover their intended defect. If a tissue expander is removed before the expanded tissues are transposed, though, all the expansion gained over time is lost and the tissues return nearly to their pre-expansion state. The most common reason for premature tissue expander removal is infection. These devices are subjected to repeated inflations of saline solution, introduced percutaneously into remote filling devices that communicate with the expander itself. Bacterial contamination of the device is thought to occur usually from the percutaneous inflation process. Once contamination is established and a biofilm forms, local infection is likely. Expander removal, with the annulment of the reconstructive effort, is needed to control the infection. A delay of a number of months is usually recommended before a new tissue expander can be inserted in the affected area. The silicone elastomer used for these devices is especially suitable for integrating with sulfate ester AF agents. Use of these agents in the manufacture of these articles may reduce the incidence of bacterial contamination, biofilm development and subsequent local infection.

Insertable devices include those objects made from synthetic materials applied to the body or partially inserted into the body through a natural or an artificial site of entry. Examples of articles applied to the body include contact lenses and stoma appliances. An artificial larynx is understood to be an insertable device in that it exists in the airway, partially exposed to the environment and partially affixed to the surrounding tissues. An endotracheal or tracheal tube, a gastrostomy tube or a catheter are examples of insertable devices partially existing within the body and partially exposed to the external environment. The endotracheal tube is passed through an existing natural orifice. The tracheal tube is passed through an artificially created orifice. Under any of these circumstances, the formation of biofilm on the device permits the ingress of microorganisms along the device from a more external anatomic area to a more internal anatomic area. The ascent of microorganisms to the more internal anatomic area commonly causes local and systemic infections.

As an example, biofilm formation on soft contact lenses is understood to be a risk factor for contact-lens associated corneal infection. The eye itself is vulnerable to infections due to biofilm production. Incorporating an antifouling agent in the contact lens itself and in the contact lens case can reduce the formation of biofilms, thereby reducing risk of infection. Sulfate ester AF agents can also be incorporated in ophthalmic preparations that are periodically instilled in the eye.

As another example, biofilms are understood to be responsible for infections originating in tympanostomy tubes and in artificial larynxes. Biofilms further reside in tracheostomy tubes and in endotracheal tubes, permitting the incursion of pathogenic bacteria into the relatively sterile distal airways of the lung. These devices are adaptable to the incorporation or the topical application of sulfate ester AF agents to reduce biofilm formation and subsequent infectious complications.

As another example, a wide range of vascular catheters are fabricated for vascular access. Temporary intravenous catheters are placed distally, while central venous catheters are placed in the more proximal large veins. Catheter systems can include those installed percutaneously whose hubs are external to the body, and those whose access ports are buried beneath the skin. Examples of long-term central venous catheters include Hickman catheters and Port-a-caths. Catheters permit the infusion of fluids, nutrients and medications; they further can permit the withdrawal of blood for diagnostic studies or the transfusion of blood or blood products. They are prone to biofilm formation, increasingly so as they reside longer within a particular vein. Biofilm formation in a vascular access device can lead to the development of a blood-borne infection as planktonic organisms disseminate from the biofilm into the surrounding bloodstream. Further, biofilm formation can contribute to the occlusion of the device itself, rendering it non-functional. If the catheter is infected, or if the obstruction within it cannot be cleared, the catheter must be removed. Commonly, patients with these devices are afflicted with serious medical conditions. These patients are thus poorly able to tolerate the removal and replacement of the device. Furthermore, there are only a limited number of vascular access sites. A patient with repeated catheter placements can run out of locations where a new catheter can be easily and safely placed. Incorporation of sulfate ester AF agents within catheter materials or application of these agents to catheter materials can reduce fouling and biofilm formation, thereby contributing to prolonged patency of the devices and minimizing the risk of infectious complications.

As another example, a biliary drainage tube is used to drain bile from the biliary tree to the body's exterior if the normal biliary system is blocked or is recovering from a surgical manipulation. Drainage tubes can be made of plastics or other polymers. A biliary stent, commonly fabricated of a plastic material, can be inserted within a channel of the biliary tree to keep the duct open so that bile can pass through it. Biliary sludge which forms as a result of bacterial adherence and biofilm formation in the biliary system is a recognized cause of blockage of biliary stents. Pancreatic stents, placed to hold the pancreatic ducts open or to drain a pseudocyst of the pancreas, can also become blocked with sludge. Biofilms are furthermore implicated in the ascent of infections into the biliary tree along a biliary drainage tube. Ascending infections in the biliary tree can result in the dangerous infectious condition called cholangitis. Incorporation of compounds of the invention in the materials used to form biliary drainage tubes and biliary stents can reduce the formation of biofilms, thereby decreasing risk of occlusions and infections.

As another example, a peritoneal dialysis catheter is used to remove bodily wastes in patients with renal failure by using fluids instilled into and then removed from the peritoneal cavity. This form of dialysis is an alternative to hemodialysis for certain renal failure patients. Biofilm formation on the surfaces of the peritoneal dialysis catheter can contribute to blockage and infection. An infection entering the peritoneal cavity is termed a peritonitis, an especially dangerous type of infection. Peritoneal dialysis catheters, generally made of polymeric materials like polyethylene, can be coated with or impregnated with sulfate ester AF agents to reduce the formation of biofilms.

As yet another example, a wide range of urological catheters exist to provide drainage of the urinary system. These catheters can either enter the natural orifice of the urethra to drain the bladder, or they can be adapted for penetration of the urinary system through an iatrogenically created insertion site. Nephrostomy tubes and suprapubic tubes represent examples of the latter. Catheters can be positioned in the ureters on a semipermanent basis to hold the ureter open; such a catheter is called a ureteral stent. Urological catheters can be made from a variety of polymeric products. Latex and rubber tubes have been used, as have silicones. All catheters are susceptible to biofilm formation. This leads to the problem of ascending urinary tract infections, where the biofilm can spread proximally, carrying pathogenic organisms, or where the sessile organisms resident in the biofilm can propagate planktonic organisms that are capable of tissue and bloodstream invasion. Organisms in the urinary tract are commonly gram-negative bacteria capable of producing life-threatening bloodstream infections if they spread systemically. Infections wherein these organisms are restricted to the urinary tract can nonetheless be dangerous, accompanied by pain and high fever. Urinary tract infections can lead to kidney infections, called pyelonephritis, that can jeopardize the function of the kidney. Incorporating sulfate ester AF agents can inhibit biofilm formation and may reduce the likelihood of these infectious complications.

A further complication encountered in urological catheters is encrustation, a process by which inorganic compounds comprising calcium, magnesium and phosphorous are deposited within the catheter lumen, thereby blocking it. These inorganic compounds are understood to arise from the actions of certain bacteria resident in biofilms on catheter surfaces. Reducing biofilm formation by the action of sulfate ester AF agents may contribute to reducing encrustation and subsequent blockage of urological catheters.

Other catheter-like devices exist that can be treated with AF agents. For example, surgical drains, chest tubes, hemovacs and the like can be advantageously treated with materials to impair biofilm formation. Other examples of such devices will be familiar to ordinary practitioners in these arts.

Materials applied to the body can advantageously employ the AF compounds disclosed herein. Dressing materials can themselves incorporate the AF compounds, as in a film or sheet to be applied directly to a skin surface. Additionally, AF compounds of the instant invention can be incorporated in the glue or adhesive used to stick the dressing materials or appliance to the skin. Stoma adhesive or medical-grade glue may, for example, be formulated to include an AF agent appropriate to the particular medical setting. Stoma adhesive is used to adhere stoma bags and similar appliances to the skin without traumatizing the skin excessively. The presence of infectious organisms in these appliances and on the surrounding skin makes these devices particularly appropriate for coating with AF agents, or for incorporating AF agents therein. Other affixation devices can be similarly treated. Bandages, adhesive tapes and clear plastic adherent sheets are further examples where the incorporation of an AF agent in the glue or other adhesive used to affix the object, or incorporation of an AF agent as a component of the object itself, may be beneficial in reducing skin irritation and infection.

These above examples are offered to illustrate the multiplicity of applications of compounds of the invention in medical devices. Other examples will be readily envisioned by skilled artisans in these fields. The scope of the present invention is intended to encompass all those surfaces where the presence of fouling has adverse health-related consequences. The examples given above represent embodiments where the technologies of the present invention are understood to be applicable. Other embodiments will be apparent to practitioners of these and related arts. Embodiments of the present invention can be compatible for combination with currently employed antiseptic regimens to enhance their antimicrobial efficacy or cost-effective use. Selection of an appropriate vehicle for bearing a compound of the invention will be determined by the characteristics of the particular medical use. Other examples of applications in medical environments to promote antisepsis will be readily envisioned by those of ordinary skill in the relevant arts.

The present invention is further illustrated by the following examples, which should not be construed as limiting in any way. The contents of all cited references including literature references, issued patents and published patent applications as cited throughout this patent application are hereby expressly incorporated by reference.

EXAMPLES

Example 1

Inhibition of Surface Attachment of Marine Bacteria by Alkyl Sulfates

Octyl sulfate is an alkyl sulfate surfactant with extensive industrial applications, and is manufactured by several large chemical companies. To investigate potential AF properties of the sulfate ester octyl sulfate, it was incorporated into an inert coating material that was then coated onto a surface to be exposed to conditions that support the formation of marine algal biofilms.

Materials and Methods

A 30% (w/v) solution of octyl sulfate in water (Stepan Chemical Co.) was evaporated to dryness under a stream of room temperature air, to recover pure octyl sulfate (FIG. 1). The dry octyl sulfate was incorporated into RTV-11 silicone polymer at a loading of 25% (wt/wt) (RTV-11 silicone, catalyst and primer obtained from General Electric). The mixture was applied to three glass slides previously primed with silicone primer, and allowed to cure to dryness. Three primed glass slides coated with pure RTV-11 served as agent-free controls. After complete drying, the absorption properties of each slide were measured using a Shimadzu UV-2101 spectrophotometer fitted with an integrating sphere. Slides were then placed in a tank of running raw seawater and allowed to incubate outdoors in natural sunlight for 26 days. Water temperature was nominally 15 C. Spectrophotometric determination of biofilm accumulation was measured on each slide periodically. Relative algal biomass was calculated as the ratio of absorption at 680 nm, contributed by chlorophyll a, to that at 750 nm, a wavelength not absorbed by chlorophyll, to correct for differences in turbidity and scattering properties of the different slides.

Results

As shown in FIG. 1, octyl sulfate incorporated into RTV-11 silicone, and then coated onto glass slides, significantly inhibited the formation of natural marine algal biofilms in natural seawater. After 26 days of incubation in running seawater, algal biofilm development on the octyl sulfate containing coatings was five fold less than that of controls lacking octyl sulfate, indicating that octyl sulfate possesses strong AF activity.

Studies were performed to evaluate the ability of the sulfate ester molecules octyl sulfate and methyl sulfate, to inhibit adhesion of the marine bacteriums *Oceanosprillum* and *Alteromonas atlantica* to glass surfaces.

Materials and Methods

*Oceanosprillum* adhesion test Each test consisted of a control set (with no sulfate esters) and sample sets containing the test molecules. The first test group consisted of a control sample set, a zosteric acid (5 mM) sample set, and an octyl sulfate (5 mM) sample set. The second test group consisted of a control sample set, a zosteric acid (5 mM) sample set, and a methyl sulfate (5 mM) sample set. Sample sets consisted of five 50 mL sterile centrifuge tubes, with each tube containing a glass microscope slide, 50 ml of artificial seawater (ASTM—American Society for testing and materials) with the dissolved sulfate ester, inoculated with an *Oceanosprillum* culture at $1 \times 10^6$ cells/mL. Sample sets were incubated at 23 C, with shaking so that the surface of the slides were horizontal. Over a 6-hour period, individual tubes were taken from the sample sets and tested for microbial adhesion.

*Alteromonas atlantica* adhesion tests. The tests consisted of a control sample set, a zosteric acid (5 mM) sample set, an octyl sulfate (5 mM) sample set, and a methyl sulfate (5 mM) set. A sample set consisted of six 60 mL sterile centrifuge tubes. Each tube contained a glass microscope slide and 50 mL of modified ASTM seawater (American Society for Testing and Materials (1986) D1141-86, ASTM, Philadelphia, Pa.) with dissolved agent, inoculated with *Alteromonas atlantica* culture to an initial cell density of $1 \times 10^6$ cells/mL. The modified seawater consisted of normal ASTM seawater ingredients, however the carbon source glycerol, was only 1000th the normal strength, 0.1 L/L instead of 100 L/L, and was void of an amino acid source (casamino acids), in order to allow enough carbon for attachment, but not for significant cell growth.

Determination of bacterial adhesion. Samples were removed from the shaker and 1 mL of 50× acridine orange stain (0.5 g/L acridine powder in water) was added to the tube. The stain was allowed to react for 4 minutes. The slides were then removed and fitted with a long cover slip and immediately counted with an epifluorescent microscope fitted with a 100× (oil) objective lens on the under side of the slide. The size of the counting field was 10×10 µm. A total of 20 counts per slide were performed and averaged to yield the number of cells per µm², which was in turn converted to cells per mm². Error was assigned at 10% which is the standard accepted error for direct counting of bacterial cells.

Results

Figure 2:
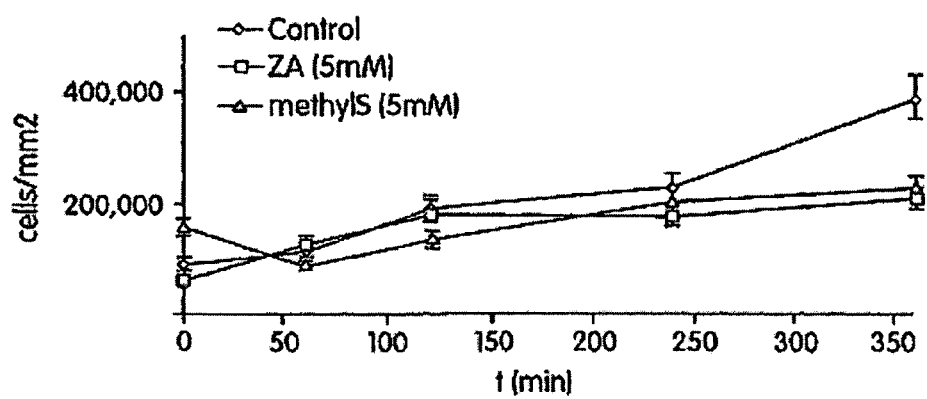
FIG. 2 is a diagrammatic representation of the results of bacterial attachment assays performed with the marine bacterium *Oceanosprillum*, cultured in the presence and absence of either zosteric acid or methyl sulfate.
Figure 3:
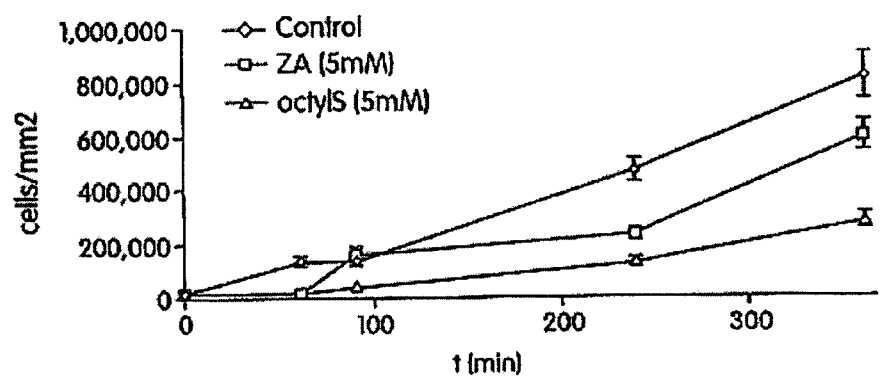
FIG. 3 is a diagrammatic representation of the results of bacterial attachment assays performed with the marine bacterium *Oceanosprillum*, cultured in the presence and absence of either zosteric acid or octyl sulfate.

As shown in FIG. 2, the presence of octyl sulfate or methyl sulfate in the medium significantly reduced bacterial adhesion to the glass slides when compared to controls in which no sulfate ester molecule was present. Methyl sulfate inhibited *Oceanosprillum* adhesion to an extent similar to the proven AF agent zosteric acid, with each compound promoting roughly a two fold reduction in bacterial attachment, relative to control. As shown in FIG. 3, octyl sulfate inhibited *Oceanosprillum* adhesion to an even greater extent than zosteric acid.

Figure 4:
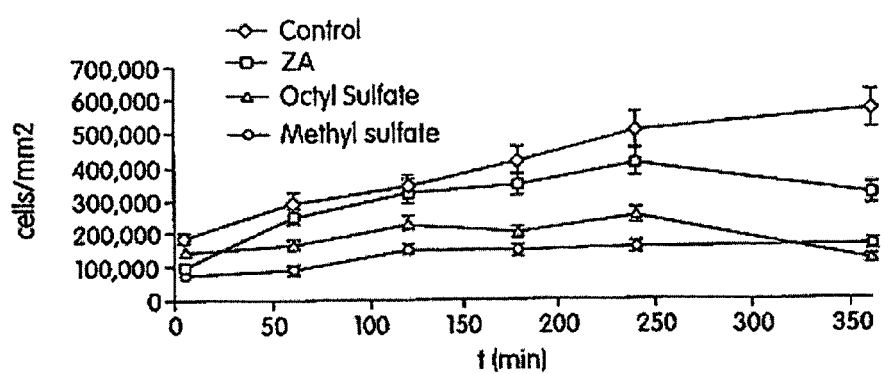
FIG. 4 is a diagrammatic representation of the results of bacterial attachment assays performed with the bacterium *Alteromonas atlantica*, performed in the presence and absence of either, zosteric acid, octyl sulfate, or methyl sulfate.

As shown in FIG. 4, the presence of dissolved zosteric acid, octyl sulfate, or methyl sulfate produced a significant reduction in the marine bacterium, *Alteromonas atlantica* adhesion relative the controls. The presence of methyl sulfate had the most dramatic effect upon adhesion, with adhesion remaining constant after 120 minutes at 150,000 cells/mm², while controls had greater than 700,000 cells/mm². Octyl sulfate also inhibited adhesion, demonstrating a slightly higher inhibitory activity than zosteric acid.

Example 2

Inhibition of Fungal Surface Attachment and Mycelial Development

To determine the effectiveness of sulfate esters at inhibiting fungal biofouling, the ability of zosteric acid to inhibit attachment of the fungus *Aureobasidium pullulans* to surfaces was examined.

Materials and Methods

*Aureobasidium pullulans* (ATCC 34261) was grown on potato-dextrose agar and harvested according to ASTM G-21-90 protocols (American Society for Testing and Materials (1986) D1141-86, ASTM, Philadelphia, Pa.). The resulting spore suspension was used to inoculate liquid culture tubes containing 35 mL of growth medium (nutrient salts with 5 mM sucrose) and 15 mM zosteric acid. Zosteric acid-free medium was prepared as a control. A sterile microscope slide was added to each tube, the tubes were sealed and placed on a rotary shaker table at room temperature. One tube was harvested each day by removing the slide and counting the number of attached spores by direct microscopic counts, as described above.

Results

Figure 5:
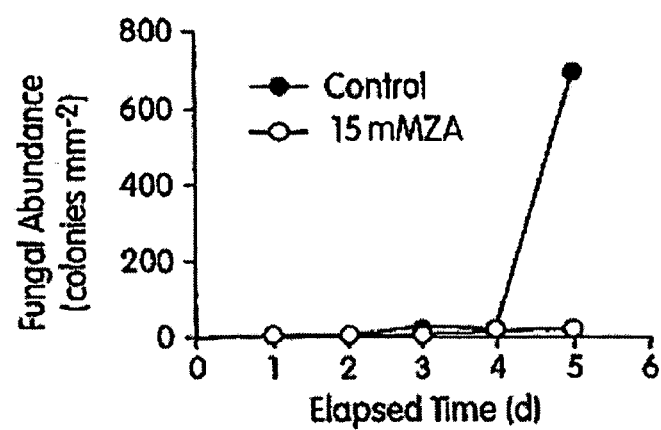
FIG. 5 is a diagrammatic representation of the results of fungal attachment and growth assays using the fungus *Aureobasidium pullulans* (a shower fungus that stains grout) grown in the presence and absence of zosteric acid, where fungal abundance represents the attachment of *A. pullulans* to the exposed surface.

Fungal spores were observed to grow in both the presence and absence of zosteric acid, as indicated by the clouding of all tubes after Day 1. However, as shown in FIG. 5, the presence of zosteric acid prevented the attachment of the fungus to the glass slides. After 5 days incubation with *A. pullalans*, less than 20 germinated fungal colonies/mm² were observed on slides incubated in the additional presence of zosteric acid, compared to more than 600 germinated fungal colonies/mm² on control slides. Furthermore, fungal colonies in the media of zosteric acid free cultures were composed of multi-cellular (>20 cells) filaments, indicative of mycelial growth. In contrast, colonies in the zosteric acid treated cultures were generally small and round, exhibiting no evidence of filamentous growth or mycelial development.

Example 3

Sulfate Esters Bind Cell Surfaces of Biofouling Organisms

To investigate the mechanism behind the AF activity of sulfate esters, polyclonal antibodies specific for the sulfate ester zosteric acid were generated (BAbCo, Berkeley, Calif.). Preliminary testing of these antibodies for cross reactivity towards related compounds lacking the sulfate ester group (cinnamic acid, ferulic acid, coumaric acid) showed no cross reactivity, suggesting that the specific domain recognized by the antibodies probably includes the sulfate ester group. These antibodies were then used to investigate whether the sulfate ester AF agent zosteric acid directly binds fouling organisms.

The marine bacterium *Shewanella putrefaciens* were grown in cultures containing zosteric acid and were subsequently examined for bound zosteric acid using immunogold staining with the antibody described above. Electron microscopic examination of immunoprobed *S. putrefaciens* detected zosteric acid molecules bound to the surface of the bacteria. Furthermore, zosteric acid was observed to be present at high incidence at the sites of cell adhesion. In contrast to these agglutination sites, the majority of the cell surfaces as well as the continuous boundaries between daughter cells in dividing chains, showed no evidence of bound zosteric acid, as indicated by a lack of immuno-gold staining. These results indicate that sulfate esters bind to the surfaces of bacterial cells and suggest a possible relationship between sulfate ester binding sites and the sites of bacterial agglutination.

Example 4

Zosteric Acid Promotes Bacterial Agglutination

To further investigate the role of sulfate esters in agglutination, the ability of sulfate esters to facilitate the agglutination of bacterial cells was investigated. Log-phase cultures grown in the presence of zosteric acid were monitored spectrophotometrically ($OD_{600}$) for growth, and for agglutination in the presence of increasing amounts of zosteric acid.

Materials and Methods

Cell Surface Binding Assays. The marine bacterium *Shewanella putrefaciens* was grown in marine broth in the presence of 16 mM zosteric acid. Dense log phase cells were harvest after 5 hours growth, and preserved in 0.5× Kamofsky's fixative (2% formaldehyde, 2.5% gluturaldehyde, 0.05 M sodium cacodylate, 0.25 M sucrose, pH 7.4) for 2 hours, and then transferred to a cacodylate buffer (0.05 M sodium cacodylate, pH 7.4) for storage. Cells were prepared for electron microscopic examination using immuno-gold staining techniques (Harlow, E. and Laine, D., Antibodies, A Laboratory Manual, Cold Spring Harbor Laboratory, 359–421; Roth et al., *J. Histochem. Cytochem.* 26: 1074–1081 (1978)). The primary antibody used in this study was an anti-zosteric acid polyclonal antibody (BAbCo, Richmond, Calif.).

Bacterial agglutination assays. Log-phase cultures of *Shewanella putrefaciens* were grown in complete seawater medium containing zosteric acid at a range of concentrations up to 20 mM. Cultures were counted for viable colony forming units at eight hours.

Results

Figure 6:
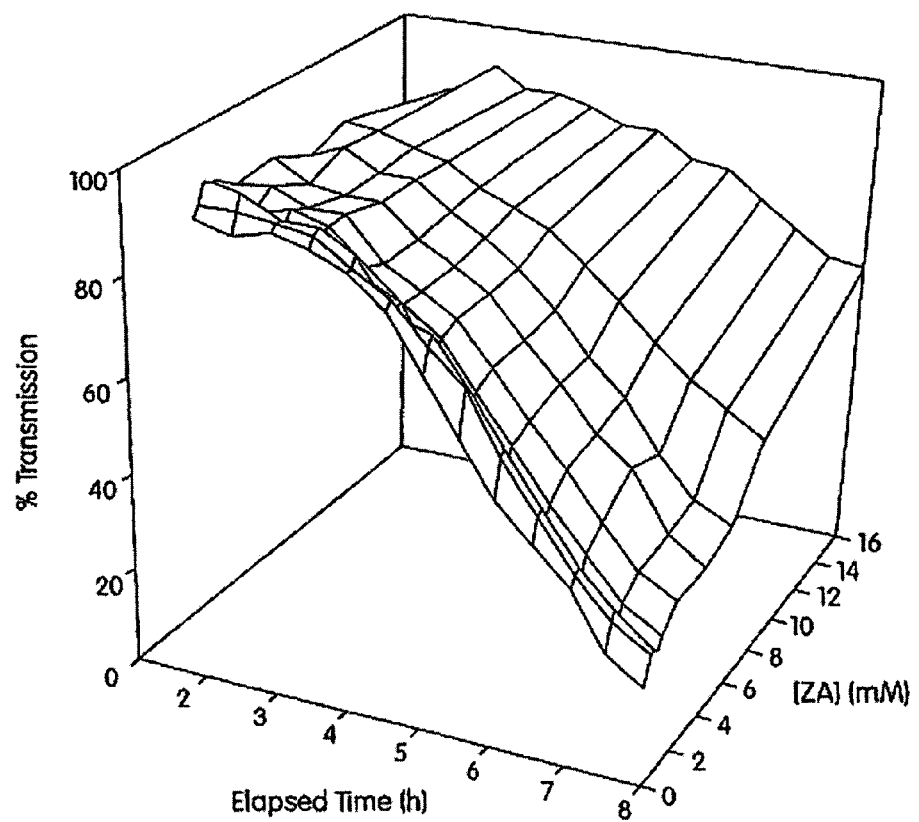
FIG. 6 is a diagrammatic representation of the results of agglutination of the bacterium *Shewanella putrefaciens* induced by the presence of increased amounts of zosteric acid, measured by the percent transmission (% T) of the liquid cultures at wavelength 600 nm. Agglutination is indicated by the concentration-dependent increase in % T of cultures grown in the presence of zosteric acid. In this case, relatively high levels of % T exhibited by the zosteric acid-exposed cultures do not reflect differences in growth, as counts of viable colony forming units exhibited no difference in cell density at eight hours.

Although zosteric acid concentrations up to 16 mM did not inhibit the growth of *S. putrefaciens* in liquid culture, the presence of zosteric acid caused significant agglutination of *S. putrefaciens* in a concentration dependent manner. The agglutination observed was visible to the naked eye, and was more quantitatively detected as a decrease in optical density absorbance in cultures containing zosteric acid (FIG. 6). Counts of viable colony forming units at eight hours revealed no difference in cell density among the different cultures, thus the observed differences in absorption resulted from differences in bacterial agglutination, not differences in growth (cell division) rates among the cultures. Thus, zosteric acid promoted cell agglutination, but did not affect cell growth.

Example 5

Zosteric Acid Binds Heparin-Sensitive Sites

To investigate the ability of sulfate esters to mediate the interaction between biological surfaces involved in erythrocyte agglutination and blood clotting, erythrocyte agglutination assays and clot formation assays were performed using the sulfate ester zosteric acid.

Materials and Methods

Red Blood Cell agglutination assays. Washed equine erythrocytes suspended in 1 mg/mL sodium citrate were placed in microtiter plates designed with wells containing hemispherical bottoms. Negative controls (no zosteric acid) were diluted in isotonic saline solution. Zosteric acid treated cells were diluted with saline containing zosteric acid at eight concentrations ranging from 0.005 to 5.0 mg/mL. Positive controls were exposed to the same range of high molecular weight heparin sulfate concentrations.

Clotting assays. Clotting time assays were performed using commercial kits (Sigma Chemical Co.) for prothrombin clotting time. Serum was harvested from 30 mL of whole human blood obtained by venous puncture using centrifugation to remove blood cells. Zosteric acid and high MW heparin were added to separate aliquots of the serum, producing concentrations from 0 to 5.0 mg/mL. Clotting times were determined for each concentration in duplicate according to the protocols provided with the kit.

Results

In agglutination studies, equine erythrocytes were significantly agglutinated by zosteric acid at concentrations as low as 0.175 mg/mL. In contrast, the presence of high molecular weight heparin produced visible agglutination only at concentrations greater than 0.75 mg/mL. This result indicates that monomeric zosteric acid is eight times more reactive with cell surface glycoproteins and polysaccharides involved in cell agglutination, than high molecular weight heparin.

Zosteric acid was also effective at preventing clot formation, as measured by the prothrombin clotting time assays (FIG. 7), although this activity was considerably less than that observed for heparin. Heparin was effective at preventing clot formation at concentrations well below 0.1 mg/ml, while zosteric acid was effective only at concentrations exceeding 10 mg/ml. The effectiveness of heparin-like anticoagulants is strongly linked to size, with high molecular weight molecules being more effective. Thus, it is not surprising that the low molecular weight zosteric acid was considerably less effective than high molecular weight heparin in mediating clot formation. A derivative of zosteric acid or another sulfate ester that is higher in molecular weight may prove more effective. Nonetheless, these results indicate that zosteric acid interacts with cell surface glycoproteins and/or polysaccharides in a manner similar to that of heparin.

Example 6

Zosteric Acid Blocks Fertilization

The data above suggests that sulfate esters interact with sulfate ester-binding receptors in a variety of systems ranging from bacteria to mammalian erythrocytes. The fusion of sperm and egg cells in invertebrate and mammalian systems also appears to be mediated by organo-sulfate molecules such as the polysaccharides fucose sulfate and heparin. In light of this, the following experiments were initiated to identify potential AF properties of sulfate esters in fertilization.

A simple sea urchin assay was used to detect and quantitate the ability of sulfate esters to block sperm-egg fusion. Sea urchin sperm was added to freshly collected eggs in the presence and absence of increasing amounts of the sulfate ester zosteric acid, and the eggs were subsequently scored for successful fertilization.

Materials and Methods

Fertilization assays. Healthy sea urchins were induced to spawn by injection with 0.5 M KCL solution. Freshly collected eggs were gently washed and resuspended in filtered sea water (FSW, pH 8.2) and aliquotted into separate tubes for fertilization assays. Zosteric acid was added to each tube from a concentrated stock dissolved in FSW (pH 8.2), along with additional FSW to ensure a constant volume in each tube. Equal amounts of sperm were added to each tube and percent fertilization was determined by direct microscopic counting. Eggs with elevated fertilization membranes were scored as fertilized. Assays were performed at sperm-limiting concentrations that allowed 95–99% fertilization in the absence of zosteric acid.

Sea urchin egg agglutination assays. Agglutination of unfertilized eggs by bindin was evaluated at the range of zosteric acid concentrations indicated in Table 1. Freshly spawned eggs were suspended in acidic seawater (pH 5) for 5 minutes to remove the outer jelly coat, and then washed 5 times in normal FSW (pH 8.2). Eggs were then transferred into plastic petri dished containing a range of zosteric acid concentrations and incubated for 15 minutes. Purified bindin (D. Epel, Stanford University) was added to the eggs at concentrations ranging from 1.2 to 12 μg/mL. The mixtures were gently agitated on a rotary shaker for 5 minutes and visually examined for agglutination. Bovine serum albumen (BSA) was used in separate assays to control for nonspecific agglutination of the dejellied eggs.

Dot blot assays. Serial dilutions of purified bindin, a covalently conjugated zosteric acid-BSA molecule, and an unconjugated mixture of free zosteric acid and BSA were pipetted onto a nitrocellulose membrane and allowed to air-dry. Standard immuno-blotting procedures were then employed to determine the reactivity between the blotted substrates and a polyclonal anti-zosteric acid antibody. The membrane was blocked in blotto (1% nonfat dry milk in phosphate buffered saline (PBS)) for 1 hour prior to probing. Probing was done in blotto for 1 hour. Primary antibody was anti-zosteric acid antibody, used at a 1:1000 dilution. Secondary antibody was alkaline phosphatase conjugated goat anti-rabbit (Southern Biotechnology Association, Inc.) and was used at a dilution of 1:1000. Rinses between probing were performed in triplicate in PBS-tween. The blot was developed in color reaction buffer (100 mM Tris, pH 9.5, 100 mM NaCl, 5 mM $MgCl_2$, 50 mg/mL Nitroblue Tetrazolium (Sigma), 50 ml/mL 5-bromo-4-chloro-3-indolyl phosphate (BCIP, Sigma)) for 20 minutes. Membranes were then transferred to stop buffer (10 mM Tris, pH 6.0, 5 mM EDTA) for 1 hour, and then transferred to freshwater, left overnight, and then dried.

Results

Figure 8:
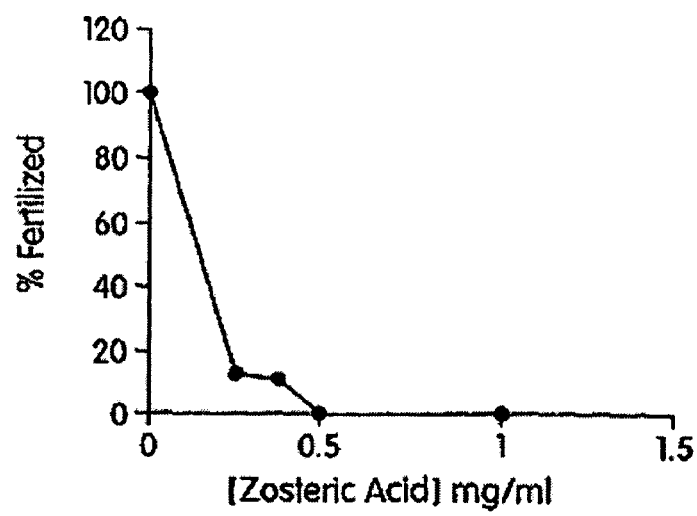
FIG. 8 is a diagrammatic representation of data measuring the effects of zosteric acid on the event of sea urchin egg fertilization. a) Dose dependent effect of zosteric acid on sea urchin fertilization. Percent fertilization represents a comparison of the number of eggs fertilized in the presence of the indicated concentration of zosteric acid, to the number of eggs fertilized under the same conditions, in the absence of zosteric acid. b) Relative effects of coumaric acid, heparin and zosteric acid at equal concentrations (1 mg/mL) on sea urchin egg fertilization.
Figure 8:
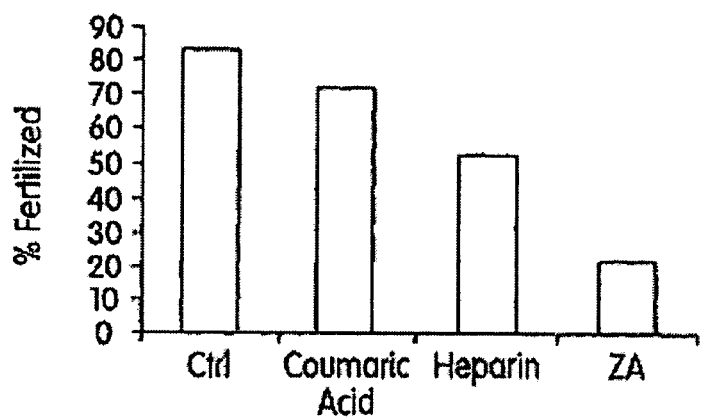
Figure 9:
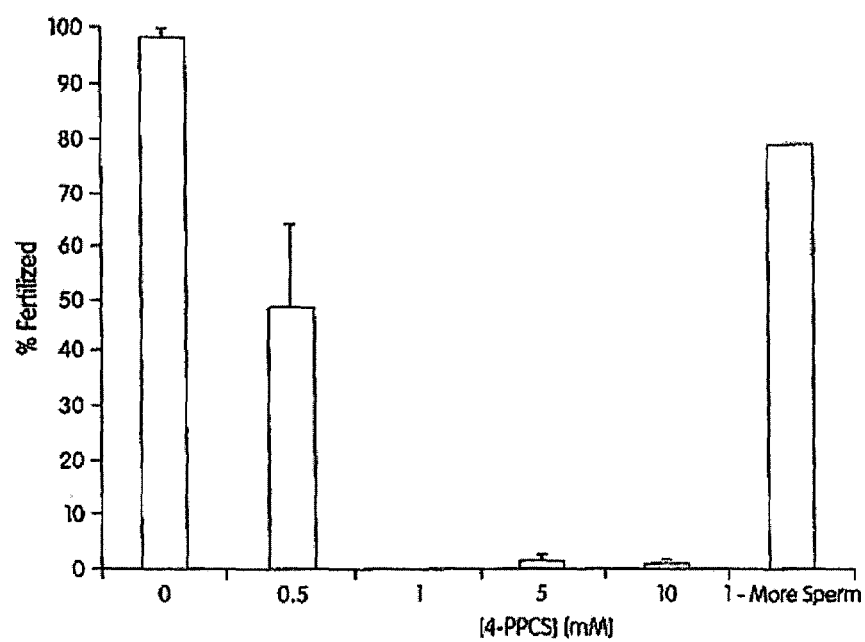
FIG. 9 is a bar graph plots the fertilization of sea urchin eggs by various concentrations of 4 t-pentyl phenyl chlorosulfate (4-PPCS).

As shown in FIG. 8a, zosteric acid had a dose-dependent effect on sea urchin egg fertilization. Concentrations higher than 0.5 mg/mL (1.5 mM) completely blocked fertilization. Re-exposure of unfertilized eggs from the highest zosteric acid treatment, to fresh sperm, after washing in sea water, resulted in the fertilization of all eggs. This result demonstrates that the zosteric acid inhibition is reversible. The presence of zosteric acid had no detected effect on sperm viability or motility. Sperm exposed to zosteric acid were observed to swim actively through the jelly layer surrounding the egg without adhering to the egg surface or elevating the egg fertilization membrane, further supporting the conclusion that the antifouling effect of zosteric acid was mediated through inhibition of sperm-egg attachment.

The effectiveness of zosteric acid (1 mg/mL) at fertilization inhibition was compared to equal mass concentrations of coumaric acid (an unsulfated zosteric acid precursor) and high MW heparin. The presence of coumaric acid had no effect on egg fertilization, while the presence of heparin reduced fertilization by approximately 50%. Zosteric acid was at least twice as effective as heparin at inhibiting fertilization, reducing fertilization to 21% at this concentration (FIG. 8b).

The ability of zosteric acid to compete for the binding of sulfate receptor sites on the egg surface was investigated in egg agglutination assays. These experiments tested the ability of zosteric acid to interfere with the binding of the bindin molecule to unfertilized sea urchin eggs. Bindin added to unfertilized eggs causes them to agglutinate by cross linking sulfate receptors that are present on the surface of the eggs. Addition of zosteric acid inhibited this agglutination in a dose dependent manner (Table 1), suggesting a competitive interaction of bindin and zosteric acid for the sulfate receptor sites on the egg surface.

TABLE 1

The effect of zosteric acid on the agglutination of sea urchin eggs by purified bindin.

| [ZA] mg $mL^{-1}$ | Agglutination |
|---|---|
| 3 | No |
| 1.5 | No |
| 0.75 | Yes |
| 0.30 | Yes |
| 0.15 | Yes |
| 0.075 | Yes |
| 0.03 | Yes |
| 0.015 | Yes |

Antibodies specific for zosteric acid (described above) exhibited strong cross reactivity with the bindin molecule in dot-blot assays, but not with other proteins, such as bovine serum albumin. This antibody cross reactivity indicates that zosteric acid and bindin share significant structural similarity at the site of antibody recognition, believed to be the sulfate moiety. Such structural similarities in the sulfate moieties between bindin and zosteric acid would explain why zosteric acid is an effective inhibitor of sea urchin fertilization.

Example 7

4 t-Pentyl Phenyl Chlorosulfate (4-PPCS) Blocks Fertilization

Figure 7:
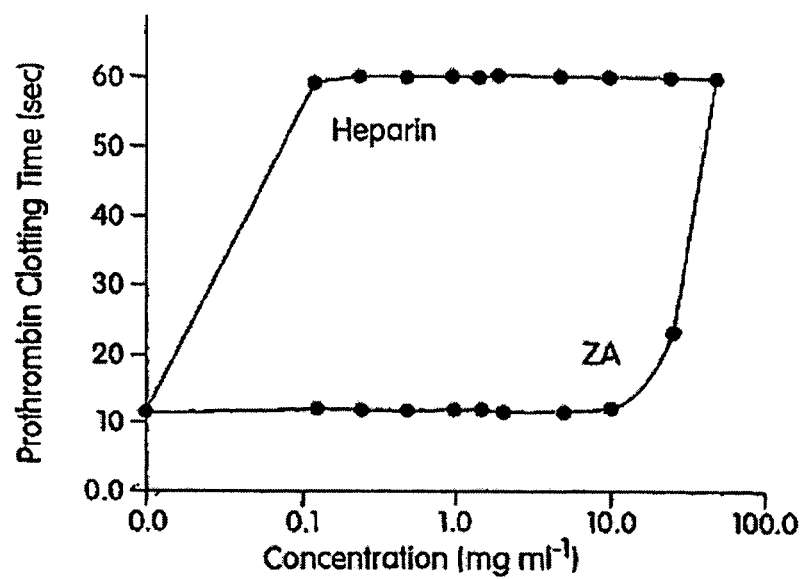
FIG. 7 is a diagrammatic representation of data from prothrombin clotting time assays which displays the clotting time of erythrocytes in the presence of high molecular weight heparin compared to the clotting time of erythrocytes in the presence of zosteric acid.

The effect of 4-PPCS on inhibiting sea urchin fertilization was performed substantially as described for zosteric acid in Example 6. As can be seen in FIG. 7, 4-PPCS was essentially 100% effective in blocking sea urchin fertilization in the range of 1–10 mM, precisely the same range as zosteric acid was effective. As also can be seen in FIG. 7, when more sperm were added to the medium, the effect of the PPCS inhibition could be washed out be exceeding the binding capacity of the 4-PPCS in solution. In contrast to most biocidal agents, contact with 4-PPCS resulted in no adverse impacts on sperm motility.

Equivalents

Those skilled in the art will recognize, or be able to ascertain using no more than routine experimentation, many equivalents of the specific embodiments of the invention described herein. Such equivalents are intended to be encompassed by the following claims.

The invention claimed is:

1. A coating comprising an effective amount of a compound represented by general structure 1:

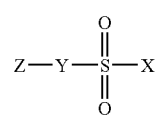

wherein
  X represents —OH, F, Cl, or Br;
  Y represents O;
  Z represents 4-(2-methylpropyl)phenyl, 4-(1,1-dimethylethyl)phenyl, 4-(1,1-dimethylpropyl)phenyl, 4-pentylphenyl, 4-(1-methyl-1-phenylethyl)phenyl, or 4-(1-methylheptyl)phenyl;
wherein when the coating is applied to a surface of an article the coating releases the compound and wherein the coating comprises a phenolic resin, silicone polymer, epoxy resin, polyamide resin, vinyl resin, elastomer, acrylate polymer, silicone resin, polyester, chlorinated rubber, polyurethane, latex, or fluoropolymer.

2. The coating of claim 1, wherein X represents —OH or Cl.

3. The coating of claim 1, wherein the coating is temporary.

4. The coating of claim 1, wherein the release rate of the compound from the surface is in the range of about 1 to about 200 $\mu g cm^2 d^{-1}$.

5. The coating of claim 1, wherein the release of the compound is a sustained release.

6. The coating of claim 1, wherein the coating is formulated as a composition selected from the group consisting of paste, gel, liquid, wax, caulk, adhesive, and paint.

7. The coating of claim 1, wherein the coating is employed as an agent selected from the group consisting of glue, cement and adhesive.

* * * * *